(12) United States Patent
Chang et al.

(10) Patent No.: US 11,357,848 B2
(45) Date of Patent: Jun. 14, 2022

(54) METHODS OF RATIONAL NICOTINE HAPTEN DESIGN AND USES THEREOF

(71) Applicant: ARIZONA BOARD OF REGENTS ON BEHALF OF ARIZONA STATE UNIVERSITY, Scottsdale, AZ (US)

(72) Inventors: Yung Chang, Tempe, AZ (US); Sidney Hecht, Phoenix, AZ (US); Joseph Leal, Phoenix, AZ (US); Viswanath Arutla, Tempe, AZ (US); Xiaowei Liu, Tempe, AZ (US); Sriram Sokalingam, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1198 days.

(21) Appl. No.: 15/863,118

(22) Filed: Jan. 5, 2018

(65) Prior Publication Data

US 2018/0125969 A1 May 10, 2018

Related U.S. Application Data

(62) Division of application No. 15/189,930, filed on Jun. 22, 2016, now Pat. No. 9,884,114.

(60) Provisional application No. 62/183,445, filed on Jun. 23, 2015.

(51) Int. Cl.

| | |
|---|---|
| *A61K 39/385* | (2006.01) |
| *C07D 401/14* | (2006.01) |
| *G16B 15/00* | (2019.01) |
| *G16B 20/00* | (2019.01) |
| *A61K 47/64* | (2017.01) |
| *G01N 33/94* | (2006.01) |
| *A61K 39/00* | (2006.01) |
| *G16B 15/30* | (2019.01) |
| *G16B 20/30* | (2019.01) |

(52) U.S. Cl.
CPC ........ *A61K 39/385* (2013.01); *A61K 39/0013* (2013.01); *A61K 47/646* (2017.08); *C07D 401/14* (2013.01); *G01N 33/946* (2013.01); *G16B 15/00* (2019.02); *G16B 15/30* (2019.02); *G16B 20/00* (2019.02); *G16B 20/30* (2019.02); *A61K 2039/6012* (2013.01)

(58) Field of Classification Search
None
See application file for complete search history.

(56) References Cited

U.S. PATENT DOCUMENTS

2015/0017201 A1    1/2015   Chang et al.

OTHER PUBLICATIONS

Cosconati et al. (2010) Virtual screening with AutoDock: theory and practice, Expert Opinion on Drug Discovery, 5:6, 597-607.*
Pentel and Lesage, New directions in nicotine vaccine design and use., Advances in Pharmacology, 2014, 69:553-80.
Pryde et al., Selection of a Novel Anti-Nicotine Vaccine: Influence of Antigen Design on Antibody Function in Mice., PLOS One, Oct. 2013, 8(10):e76557(16 pages).
Collins and Janda, Investigating Hapten Clustering as a Strategy to Enhance Vaccines against Drugs of Abuse., Bioconjugate Chemistry, 2014, 25:583-600.
Lockner et al., A Conjugate Vaccine Using Enantiopure Hapten Imparts Superior Nicotine-Binding Capacity., Journal of Medicinal Chemistry, 2015, 58:1005-11.

* cited by examiner

*Primary Examiner* — Michael L Borin
(74) *Attorney, Agent, or Firm* — Quarles & Brady LLP

(57) ABSTRACT

Provided herein are methods for rational design of nicotine haptens. More particularly, provided herein are methods for designing, selecting, and synthesizing nicotine haptens and nicotine hapten conjugates. Also provided herein are novel nicotine haptens and methods for using nicotine haptens to treat nicotine addiction.

6 Claims, 14 Drawing Sheets

FIG. 8

| Nic-Haptens | $IC50_{HP}/IC50_{Nic}$ ratio |
|---|---|
| 52 | 0.006 |
| 45 | 0.007 |
| 138 | 0.009 |
| 1' | 0.02 |
| 139 | 0.09 |
| 93 | 0.2 |
| 97 | 0.4 |
| 140 | 0.46±0.25 |
| 140M | 0.06±0.02 |
| 137 | 1.6±0 |
| 146 | 5.2±0.2 |
| 142 | 11.5±11 |
| 145 | 33±4 |

FIG. 10

| Nic-Haptens | IC50$_{HP}$/IC50$_{Nic}$ ratio | IC50$_{HP}$/IC50$_{H\text{-}P\text{-}SA}$ ratio |
|---|---|---|
| 138 | 0.009 | 35 |
| 1' | 0.02 | 77 |
| 139 | 0.09 | 174 |
| 93 | 0.2 | 185 |
| 97 | 0.4 | 423 |
| 140 | 0.46 ± 0.25 | 445 ± 27 |
| 140M | 0.06 ± 0.02 | 168 ± 4 |
| 137 | 1.6 ± 0 | 659 |

FIG. 12

| Hapten | Post 2$^{nd}$ Immunization | | | Post 3$^{rd}$ Immunization | | |
|---|---|---|---|---|---|---|
| | Titer | IC50 (uM) | Quality Index | Titer | IC50 (uM) | Quality Index |
| 138 | 17,651 ± 13,646 | 225 ± 165 | 78 | 100,713 ± 22,607 | 12.3 ± 13.7 | 8,188 |
| 140 | 12,685 ± 10,941 | 27 ± 25 | 470 | 87,766 ± 23,249 | 1.2 ± 0.4 | 73,138 |
| 1' | 1,284 ± 1,002 | 67 ± 54 | 19 | 31,112 ± 33,413 | 10.1 ± 8.6 | 3,080 |

METHODS OF RATIONAL NICOTINE HAPTEN DESIGN AND USES THEREOF

CROSS-REFERENCE TO RELATED APPLICATIONS

This application is a divisional of U.S. patent application Ser. No. 15/189,930, filed Jun. 22, 2016, which claims the benefit of U.S. Provisional Patent Application No. 62/183,445, filed Jun. 23, 2015, each of which is incorporated herein by reference as if set forth in its entirety.

STATEMENT REGARDING FEDERALLY SPONSORED RESEARCH

This invention was made with government support under R01 DA035554 awarded by the National Institutes of Health. The government has certain rights in the invention.

BACKGROUND OF THE INVENTION

1. Field of the Invention

The present invention relates to methods for rationally designing nicotine haptens. More particularly, the present invention relates to the design process, to the selection and synthesis of nicotine haptens and nicotine hapten conjugates, and to their uses for nicotine vaccines.

2. Background

Cigarette smoking causes various types of diseases with high morbidities and mortality, but smoking cessation is difficult due to the addictiveness of nicotine. Nicotine molecules enter the brain within seconds after smoke inhalation, where it triggers the brain's response to rewarding stimuli and consequently establishment of addiction. Despite extensive efforts and resources directed toward the development of cessation interventions, smoking remains a major public health problem. Nicotine antibodies have preventive and therapeutic potential to curb this addictive behavior. Nicotine antibodies bind to nicotine in the bloodstream and decrease the amount of nicotine that reaches the brain. Passive transfer of nicotine-specific monoclonal antibodies offers control over nicotine antibody dose, but this therapeutic approach is expensive and has a relative short duration of action.

Nicotine vaccines have emerged as a potentially promising treatment to reduce tobacco dependence by eliciting the production of anti-nicotine antibodies that can block nicotine transfer into the brain. Standard nicotine vaccines are based on conjugates comprising a nicotine hapten linked to a protein. Nicotine haptens using linkers of various lengths and rigidities have been created, but few have been shown to significantly improve anti-nicotine immune responses and, to date, clinical trials of nicotine vaccines have been unsuccessful. Therefore, there remains a need in the art for improved methods for designing nicotine haptens that the production of anti-nicotine antibodies and improved therapeutic methods for treating nicotine addiction.

SUMMARY OF THE INVENTION

In a first aspect, provided herein is a method for obtaining a nicotine hapten capable of eliciting an immune response specific to nicotine. The method can comprise or consist essentially of (a) providing three-dimensional structural information of an immunogenic carrier; (b) selecting functional groups or small molecule fragments predicted to bind to free nicotine at an immunogenic carrier binding site, wherein a functional group or small molecule fragment is selected if indicated to exhibit higher binding energy for free nicotine than for the immunogenic carrier; and (c) linking the selected functional group or small molecule fragment in a single compound, wherein the compound is a nicotine hapten that, when conjugated to the immunogenic carrier, elicits production of anti-nicotine antibodies having an affinity index greater than 0.02 and less than or equal to 1. Selecting can comprise using a computer having a non-transitory computer-readable storage medium containing programming to perform a fitting operation and to determine one or more binding energy parameters between nicotine and a binding site of the immunogenic carrier. The method can further comprise analyzing results of the fitting operation to characterize the association between nicotine and the binding pocket. The method can further comprise synthesizing or obtaining the compound; and evaluating the compound for its ability to compete with free nicotine for binding. Evaluating can comprise performing an indirect competitive enzyme-linked immunosorbent assay (ELISA). The hapten can comprise nicotine or a nicotine derivative. The immunogenic carrier can be a streptavidin.

In another aspect, provided herein is a nicotine hapten comprising a structure selected from the group consisting of:

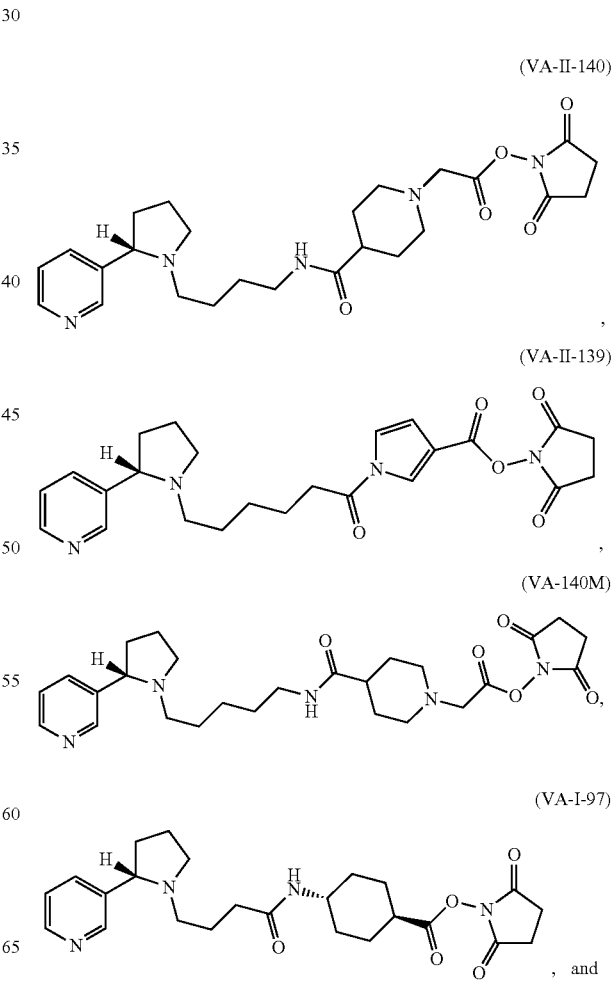

, and (VA-93)

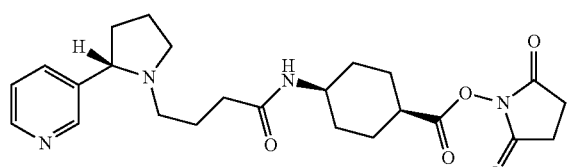

In another aspect, provided herein is a nicotine hapten conjugate comprising a nicotine hapten and an immunogenic carrier linked to the nicotine hapten, wherein the conjugate is an immunogen capable of eliciting production of antibodies having an affinity index greater than 0.02 and less than or equal to 1.

The nicotine hapten can comprise nicotine or a nicotine derivative. The nicotine hapten can have a structure selected from the group consisting of:

(VA-II-140)

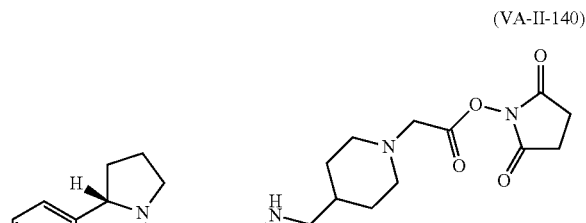

(VA-II-139)

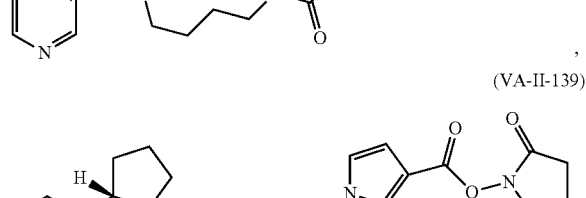

(VA-140M)

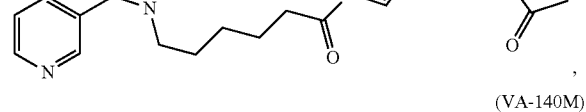

(VA-I-97)

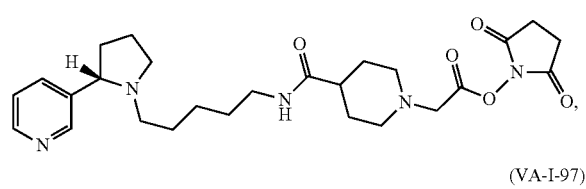

, and (VA-93)

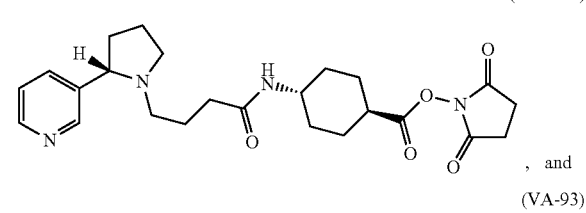

.

The nicotine hapten can have the structure:

(VA-II-140)

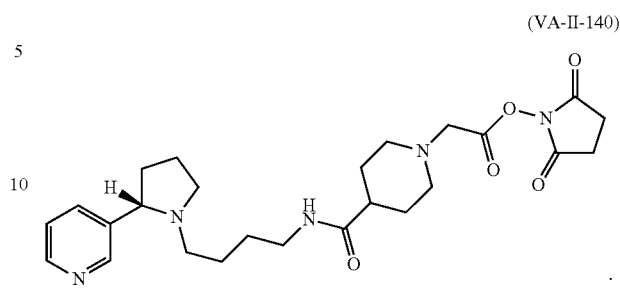

.

In another aspect, provided herein is a therapeutic composition capable of eliciting an immune response to nicotine, the composition comprising at least one nicotine hapten conjugate as provided herein. The composition can further comprise an adjuvant bound to the nicotine hapten conjugate.

In another aspect, provided herein is a method for eliciting an immune response in a subject, the method comprising administering to the subject a composition as provided herein.

These and other features, aspects, and advantages of the present invention will become better understood upon consideration of the following detailed description, drawings and appended claims.

BRIEF DESCRIPTION OF THE DRAWINGS

FIG. 8 is a table presenting binding affinity data ($IC_{50}$) for nicotine (Nic)-specific monoclonal antibodies (mAb) to nicotine haptens (Nic-HP) versus free nicotine.

FIG. 10 is a table presenting relative binding activities of mAb to Nic-HP versus nicotine-streptavidin conjugates (Nic-SA). Half inhibitory concentration ($IC_{50}$) of each hapten or free nicotine is determined by competition ELISA. The ratios between hapten $IC_{50}$ ($IC50_{HP}$) and free nicotine $IC_{50}$ ($IC50_{Nic}$) is defined as relative affinity index and calculated to compare the binding activity of various haptens to the nicotine-specific monoclonal antibody 5F3. The ratios between $IC50_{HP}$ and hapten-streptavidin $IC_{50}$ ($IC50_{HP-SA}$) is calculated to estimate the effect of SA on the interaction between hapten and monoclonal antibody 5F3.

FIG. 12 is a table demonstrating changes of anti-nicotine antibody level and relative binding affinity to free nicotine in mouse serum at 15 days after second and 40 days post third immunization. Mice were immunized s.c. with hapten-SA-CpG vaccines three times. Anti-nicotine antibody titer and binding affinity of serum to free nicotine were measured by ELISA and competition ELISA, respectively, after second and third immunization. The quality index is defined as the ratio between titer and corresponding $IC_{50}$ (µM) as a parameter to compare the antibody quality. Both anti-nicotine titers and binding affinity in all three groups increases after third immunization compared to that after second immunization. Group of 140-SA-CpG is highlighted to emphasize the drastic increase of antibody quality induced by 140 hapten-SA.

INCORPORATION BY REFERENCE

Figure 1:
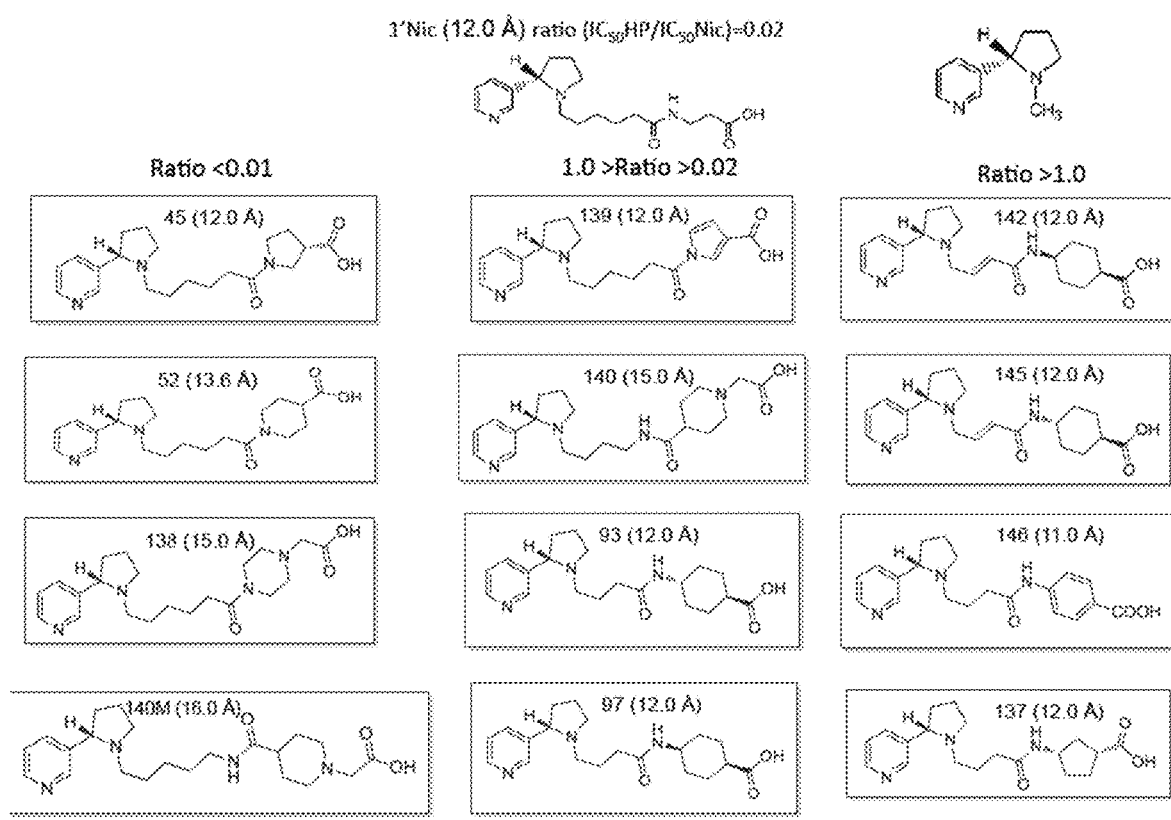
FIG. 1 shows the chemical structures of exemplary nicotine haptens.
Figure 2:
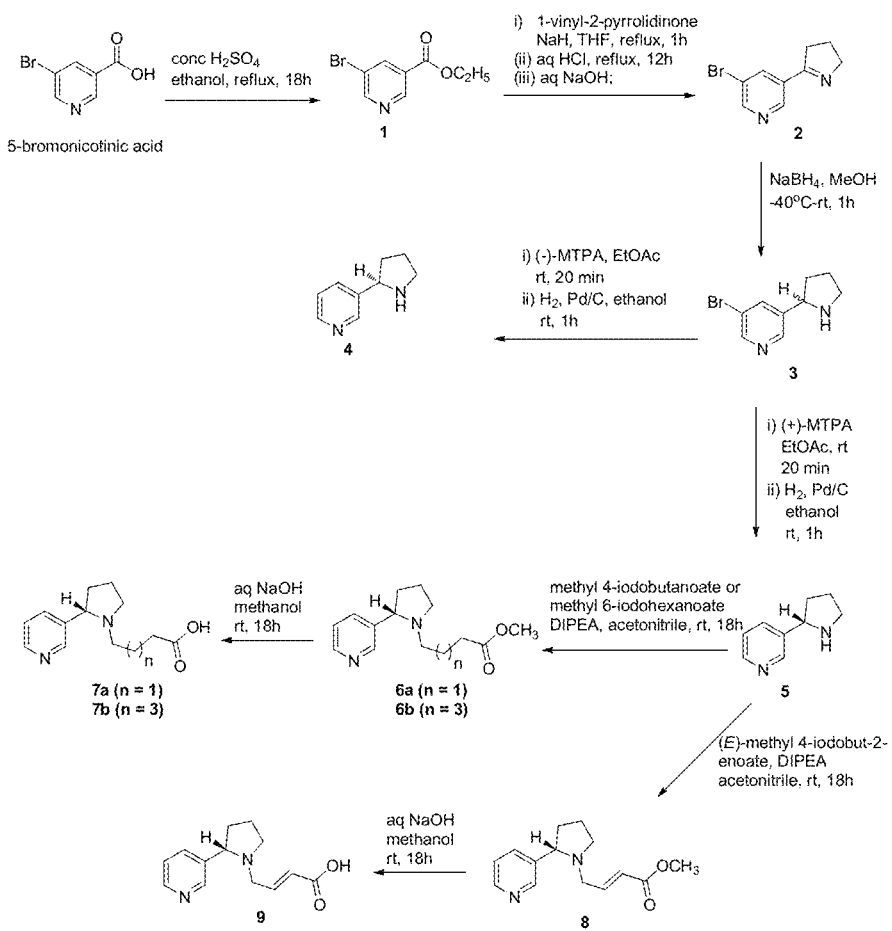
FIG. 2 shows a scheme of hapten synthesis from 5-bromonicotinic acid.
Figure 3:
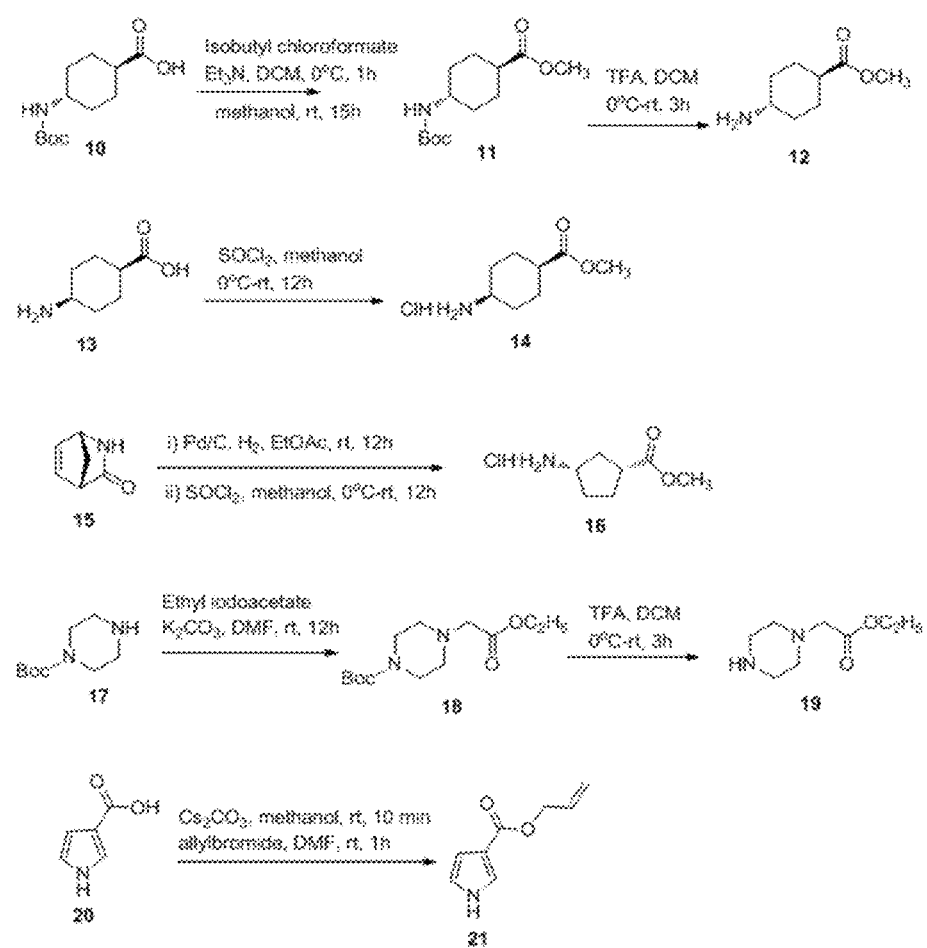
FIG. 3 shows hapten synthesis schemes for compounds 10-21.
Figure 4:
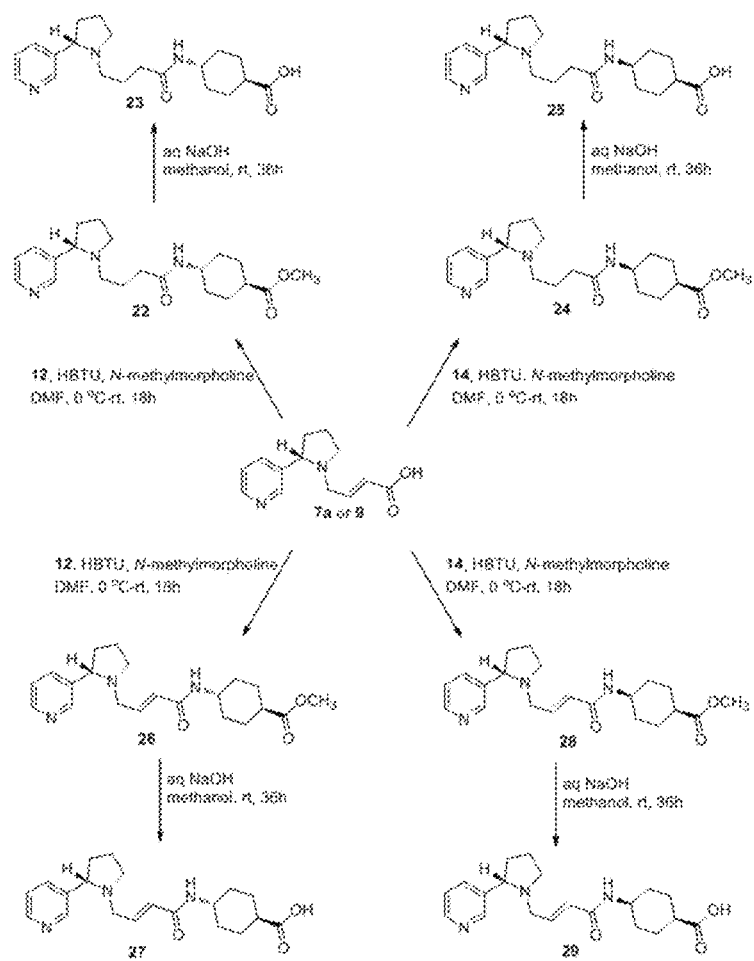
FIG. 4 shows hapten synthesis schemes for compounds 22-29.
Figure 5:
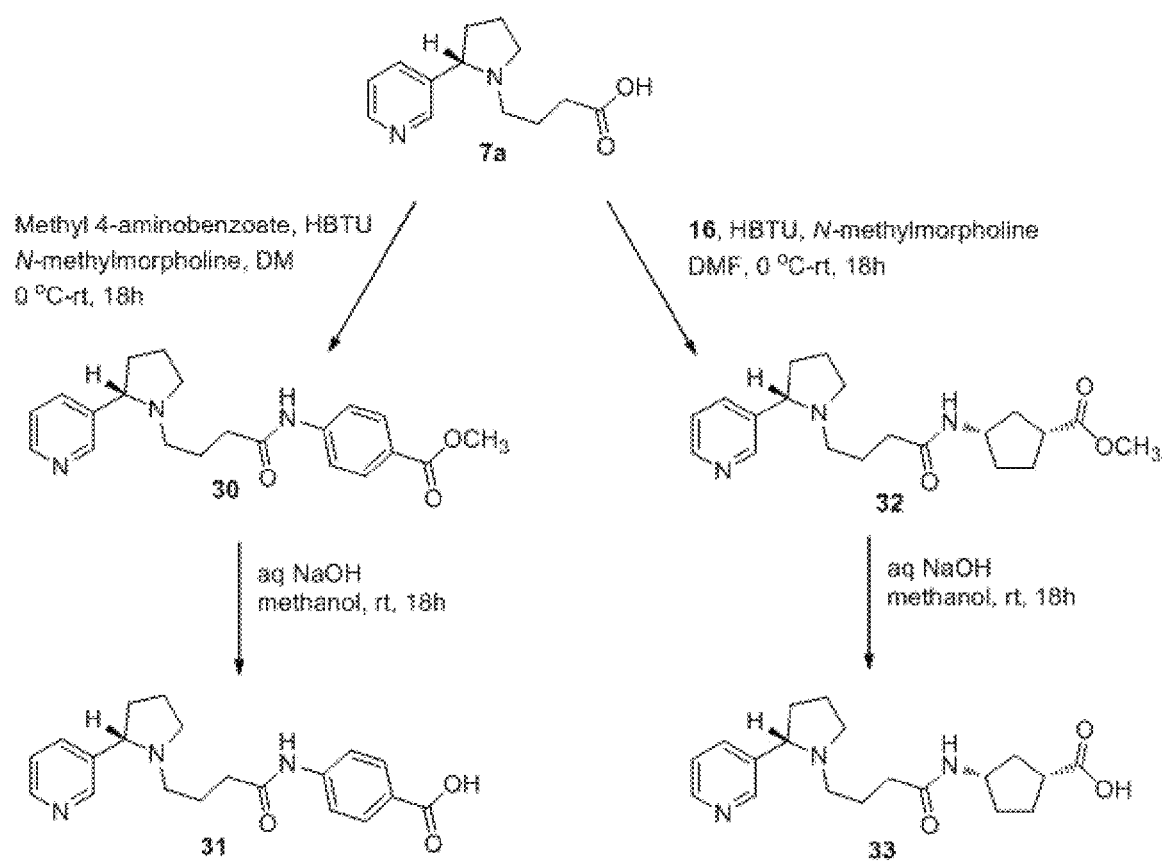
FIG. 5 shows hapten synthesis schemes for compounds 30-33.
Figure 6:
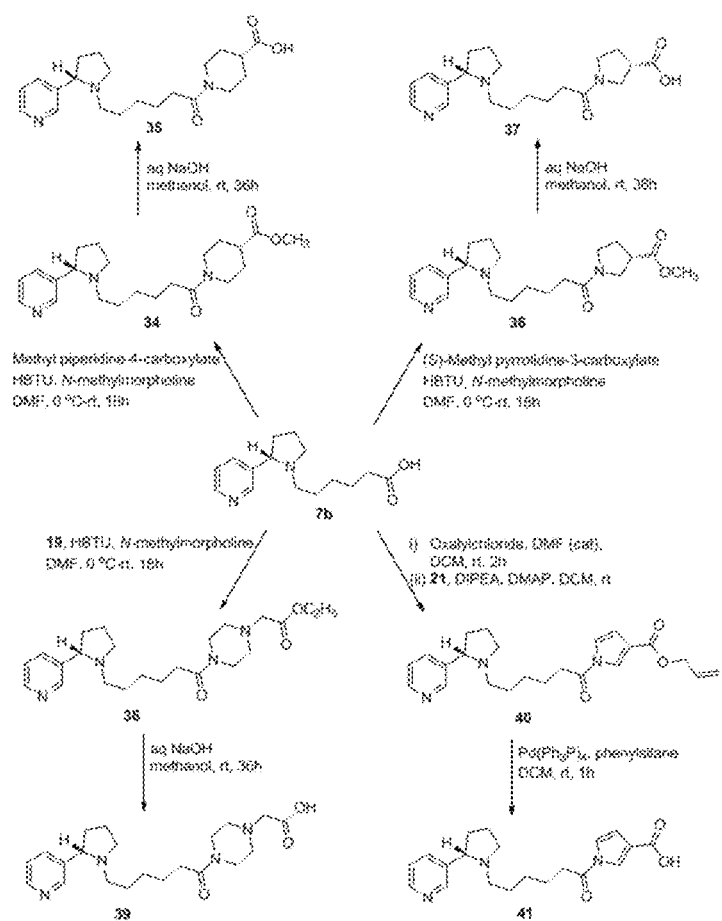
FIG. 6 shows hapten synthesis schemes for compounds 34-41.
Figure 7:
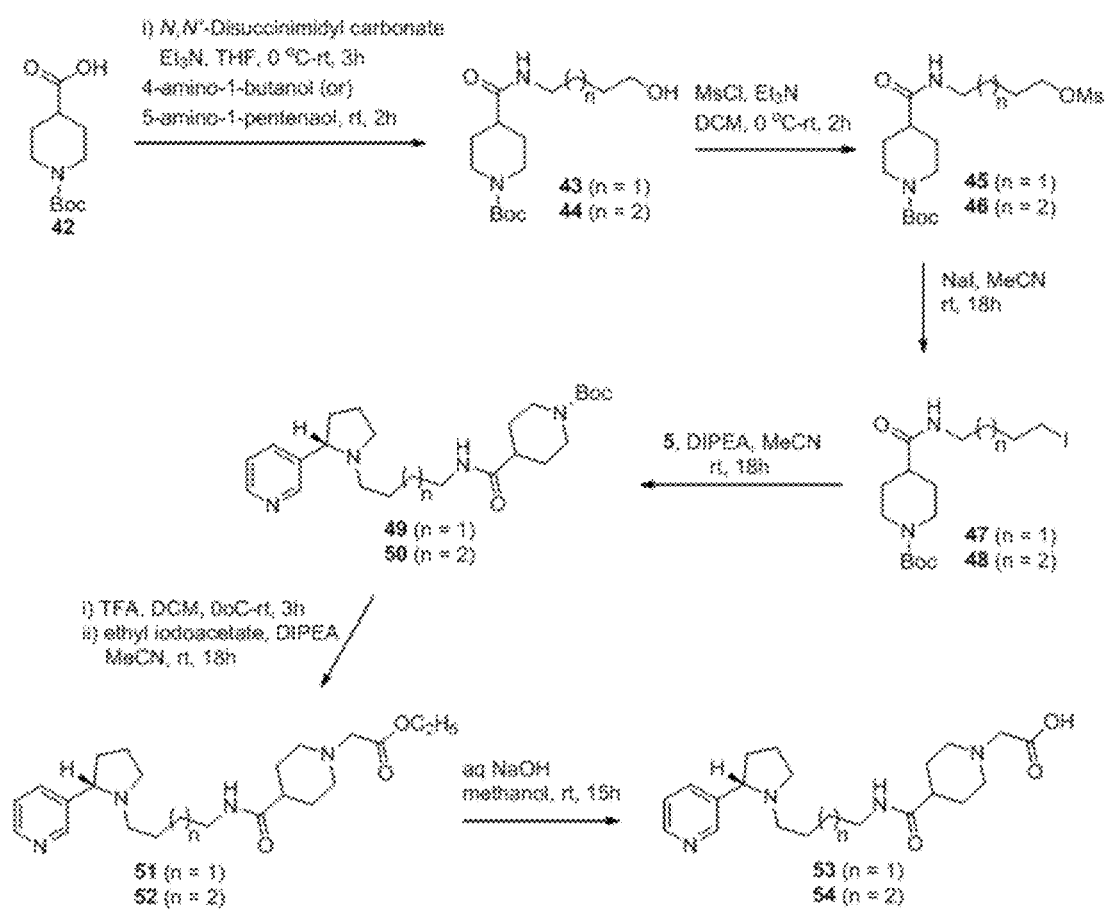
FIG. 7 shows hapten synthesis schemes for compounds 42-54.
Figures 9A, 9B, 9C:
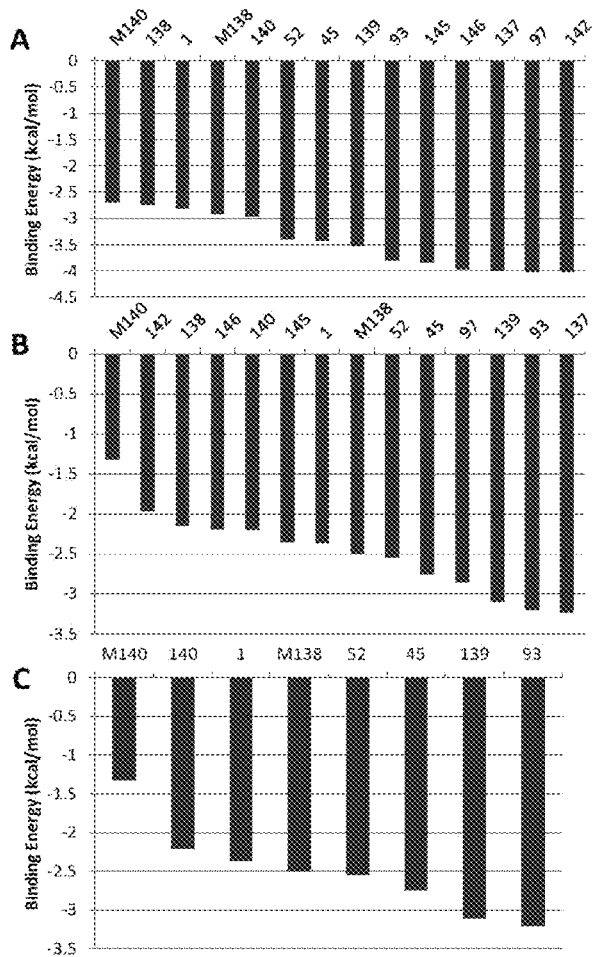
FIGS. 9A-9C are graphs representing molecular interactions between nicotine haptens and streptavidin to rank the accessibility of conjugated haptens to a Nic-specific antibody. The binding energy (kcal/mol) values predicted using the AutoDock4 docking algorithm for the interactions between nicotine haptens and streptavidin were averaged for four lysine positions of streptavidin and plotted in the order of nicotine haptens having higher binding energy considered better in this study to lower binding energy. (A) The lowest binding energy conformation of nicotine haptens towards streptavidin irrespective of the presence of conformations with expected conjugation, whereas (B) the binding energy of those which showed the expected conjugatable conformation of nicotine haptens on to streptavidin and (C) the binding energy of nicotine haptens that showed expected conjugatable conformation at all four lysine positions on streptavidin.
Figure 11:
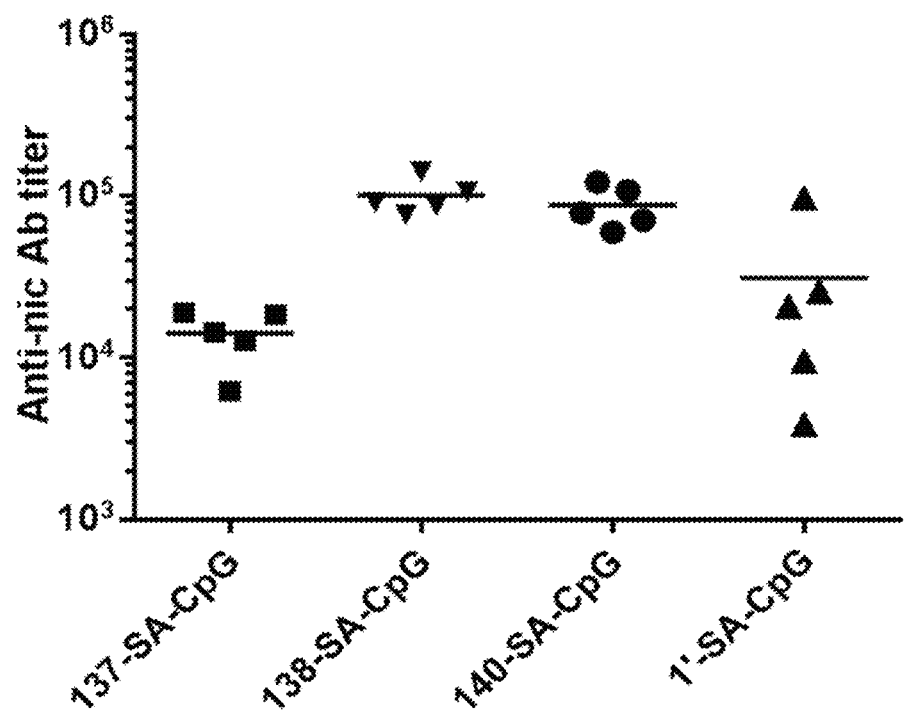
FIG. 11 is data for anti-nicotine antibody levels in mouse serum. Balb/c mice were immunized s.c. with various hapten-SA-CpG vaccines for three times and blood was collected from mouse cheek vein at 40 days post the third immunization. Serum anti-nicotine antibody titer is analyzed by ELISA. Nunc Maxisorp 96-well plates were coated with individual hapten-conjugated BSA, and the monoclonal antibody 5F3 is included as standard on each plate. Antibody titer is defined as the dilution fold of each serum when the absorbance reaches to the half maximum absorbance of 5F3 standard. Each dot in the graph represents one mouse, and the mean titer of each group is shown as a bar. Group 138 and 140 shows higher anti-nicotine titer compared to 137 and 1' groups.
Figure 13:
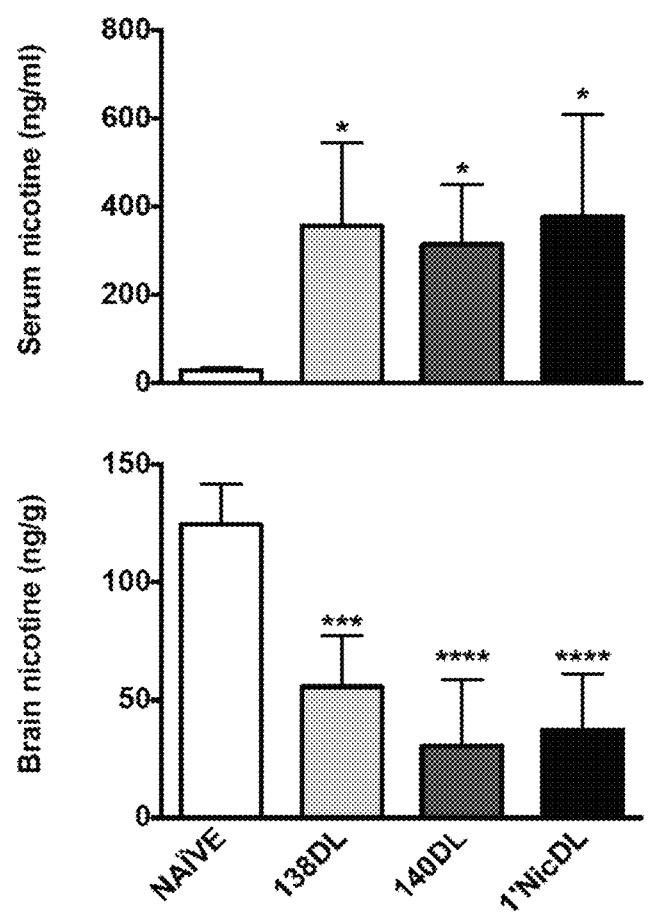
FIG. 13 demonstrates functional efficacy of nicotine vaccines as characterized by the distribution of s.c. injected nicotine in mouse serum and brain tissue (n=5). Ten days after the final challenge with hapten-SA, mice were injected s.c. with 0.1 mg/kg nicotine dissolved in PBS. Mice were decapitated 4 min later, and the brain and blood were collected for nicotine concentration analysis by gas chromatography. Brain nicotine concentrations were corrected for brain blood content. Non-immunized mice were included as naïve control groups. * represents $p<0.05$, * represents $p<0.001$, and ** represents $p<0.0001$ compared to naïve mice, as measured by one-way ANOVA with Dunnett's correction.

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

I. Terms and Abbreviations

Unless defined otherwise, all technical and scientific terms used herein have the same meaning as commonly understood by one of ordinary skill in the art to which this invention belongs. The practice of the techniques described herein may employ, unless otherwise indicated, conventional techniques and descriptions of organic chemistry, polymer technology, biochemistry, and sequencing technology, which are within the skill of those who practice in the art.

As used herein and in the appended claims, the singular forms "a," "an," and "the" include plural referents unless the context clearly dictates otherwise. As used herein, the term "substantially" as in, for example, the phrase "substantially all peptides of an array," refers to at least 90%, preferably at least 95%, more preferably at least 99%, and most preferably at least 99.9%, of the peptides of an array. Other uses of the term "substantially" involve an analogous definition.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

II. Overview

The compositions and methods provided herein are based, at least in part, on the discovery of improved methods for designing nicotine haptens. In particular, the inventors identified valuable parameters to guide rational hapten linker design and developed hapten-protein conjugates having improved immunogenicity and vaccines that elicit high-quality anti-nicotine (anti-Nic) antibody responses. Thus, the present invention overcomes the problems associated with known methods of hapten design by providing methods for designing conjugate nicotine haptens that, upon vaccination, specifically elicit antibodies having high binding affinity to free nicotine and capable of achieving therapeutically effective serum antibody titers, but having minimal affinity for hapten linkers or carrier proteins.

III. Methods

Accordingly, in a first aspect, provided herein is a method of obtaining a nicotine hapten capable of eliciting an immune response specific to nicotine. The method comprises designing and selecting candidate nicotine hapten conjugates. As used herein, the term "hapten" refers to a small molecule that is substantially incapable of being immunogenic on its own but is immunogenic when conjugated to a higher molecular weight carrier. As used herein, the term "hapten conjugate" refers to compound formed by the union of a hapten and at least one other compound. Examples of hapten conjugates include, but are not limited to, hapten-antibody conjugates, hapten-polypeptide conjugates, hapten-linker-polypeptide conjugates, and labeled probes. Generally, conjugates are formed by joining, bonding, or otherwise linking one molecule to another molecule to make a larger molecule. For example, a hapten can be covalently attached to another molecule such as a protein, antibody, nucleic acid, or lectin. In some cases, the protein is an avidin such as streptavidin. Streptavidin (SA) is a protein of bacterial origin that specifically binds biotin to the substantial exclusion of other small molecules that might be present in a biological sample.

Exemplary haptens for use according to the methods as provided herein include drugs, hormones, and toxins, but are not limited to these specific haptens. Any small molecule for which a vaccine would be useful may be used according to the methods provided herein. In exemplary embodiments, the small molecule is a drug of addiction or abuse such as, for example, nicotine, cocaine, or heroin. In other cases, haptens can be peptides, glycosylated peptides, metabolites, vitamins, hormones, prostaglandins, and toxins.

In a first aspect, provided herein is a method for obtaining a nicotine hapten capable of eliciting an immune response specific to nicotine. The method comprises the following steps: (a) estimating the length and rigidity of hapten linkers, according to their chemical structures. These haptens are ranked based on their rigidity, from high to low. The method further comprises (b) determining the accessibility of nicotine to an anti-nicotine antibody (e.g., monoclonal anti-nicotine antibody 5F3) by competition ELISA in comparison to binding of the antibody to free nicotine to derive an affinity index (ranging from 0.004 to >1), which is somewhat inversely correlated with the extent of the estimated rigidity; (c) providing three-dimensional structural information of an immunogenic carrier; (d) selecting functional groups or small molecule fragments predicted to bind to free nicotine at an immunogenic carrier binding site, wherein a functional group or small molecule fragment is selected if indicated to exhibit higher binding energy for free nicotine than for the immunogenic carrier; and (e) linking the selected functional group or small molecule fragment in a single compound. Preferably, the compound is a nicotine hapten that, when conjugated to the immunogenic carrier, elicits production of anti-nicotine antibodies having an affinity index greater than 0.004 and less than or equal to 1. More preferably, the affinity index is greater than 0.002 and less than 1.

As used herein, the term "rigid" refers to a molecule's propensity to adopt a defined conformation in preference to a variety of competing conformations. Such rigidity can be imparted by a variety of molecular features that provide a bias in favor of a local conformation about a molecular skeleton. The term "rigidity" also refers to the degree of flexibility of the molecule and includes the terms "flexible," semi-rigid," "rigid," and all variations in between.

To select a chemical structure that structurally mimics a target molecule (e.g., nicotine), it is advantageous to analyze three-dimensional structural information. Such analysis can involve performing molecular modeling. Generally, molecular modeling techniques are useful for de novo drug design. In some cases, molecular modeling is computer-aided molecular modeling. As used herein, "computer-aided molecular modeling" refers to computer program-assisted analysis of properties relevant to antigen-antibody recognition including, without limitation, three-dimensional polypeptide conformations, electrostatic potential isosurfaces, and steric and electrostatic fields. In some cases, molecular modeling involves the identification of functional groups or small molecule fragments that can interact with the binding surface of nicotine and exert a complement-inhibiting biological effect. Once such functional groups or fragments are identified, they are linked into a single compound using bridging components having suitable size and geometry to fit a binding site on nicotine and exert a biological effect. Computer programs useful for designing geometrically appropriate links and bridges for functional groups are known in the art and are preferred over manual techniques for use in the present invention. For example, a docking software program such as AutoDock4 and its accompanying graphical user interface, AutoDockTools, can be used according to a method provided herein. AutoDock programs are available at autodock.scripps.edu and at mgltools.scripps.edu on the World Wide Web.

Selection of functional groups can comprise performing analysis of docking conformations to determine one or more binding energy parameters between nicotine and a binding site of the immunogenic carrier. As used herein, the terms "binding pocket" and "binding site" are used interchangeably and refer to a region of a molecule or molecular complex, that, as a result of its shape, favorably associates with another chemical entity or compound.

In some cases, computational means are employed to analyze three-dimensional structural information. For example, a software program operated by a computer having a non-transitory computer-readable storage medium containing the program can be used to analyze the structural information and characterize the association between nicotine and the binding pocket. In exemplary embodiments, such computer-aided molecular modeling utilizes three-dimensional macromolecular structural information obtained from experimental methodologies such as X-ray crystallography and nuclear magnetic resonance (NMR) spectroscopy. Macromolecular structural information can be compiled in a database. Preferably, molecular modeling includes consideration of any perturbations in the three-dimensional conformation of the hapten, as well as concomitant changes in its electronic distribution, that can occur when a small molecule such as nicotine is conjugated to a carrier protein. Generally, small molecules that are generally too small to induce an immune response can be conjugated to a carrier protein by using a linker. However, introduction of a linker or spacer arm between the hapten and carrier protein can disturb the hapten's three-dimensional conformation. Accordingly, it is preferable that selection of hapten candidates comprise molecule modeling of candidates having an attached linker or spacer. By including the linker or spacer arm in computational modeling, it is possible to discern possibly effects on the hapten resulting from a spacer or linker or conjugation chemistry.

In further steps, methods provided herein comprise selecting one or more functional groups or small molecule fragments indicated to bind more strongly to the target molecule (e.g., nicotine) than to a non-target molecule. Selecting can involve analysis of calculations, in some cases made by a computer or person. Relevant calculations can include, without limitation, calculating theoretical geometries and electronic distributions, as well as theoretical pKa values for deprotonation enthalpy (DPE) and formation enthalpy (HO).

In preferred embodiments, haptens designed and obtained according to methods provided herein have intermediate binding affinity, i.e., their affinity index smaller than 1, but larger than 0.02. Haptens having such an affinity index are considered to be good hapten candidates as they have a balanced influence of the linker effect. As used herein, a hapten having an intermediate index is a hapten capable of eliciting production of antibodies that compete with free nicotine molecules but that exhibit no cross-reactivity to non-active hapten components. Percent cross-reactivity is defined as (50% inhibition of control ($IC_{50}$) of the target analyte/$IC_{50}$ of another compound)×100. Preferably, cross-reactivity calculations are performed using $IC_{50}$ values with units of moles (e.g., nmol/mL$^{-1}$ or pmol/mL$^{-1}$). Exemplary nicotine haptens are represented in FIG. 1.

Preferably, anti-nicotine antibodies bind to the hapten and any desired pharmacologically active metabolites. In some cases, affinity and cross-reactivity profiles of each hapten-elicited antibody is determined using any appropriate assay such as a radioimmunoassay. As used herein, "determining" means quantitatively analyzing for the amount of a substance. Preferably, determining comprises analyzing the $IC_{50}$ value (meaning "50% inhibition of control") for inhibition of free nicotine for antibodies generated against the nicotine hapten.

In preferred embodiments, selecting a structure that structurally and electronically mimics the target molecule further comprises performing an enzyme-linked immunosorbent assay (ELISA) to identify a hapten having an intermediate index. For example, an ELISA can be performed with plates coated with nicotine hapten conjugated to different carrier molecules to avoid selecting carrier molecule-reactive antibodies. In some cases, the ELISA is an indirect competitive ELISA.

Methods provided herein can further comprise synthesizing or obtaining the compound; and evaluating the compound for its ability to compete with free nicotine for binding. To elicit an antibody response to a hapten, it typically is covalently bound to a higher molecular weight molecule such as a carrier protein, and the complex will elicit the production of antibodies that recognize the hapten. In some cases, the interaction between a hapten and second molecule is direct. In other cases, the interaction involves at least one other molecule, e.g., a linker, spacer, or coupling agent. As used herein, the terms "linker," "spacer," and "coupling agent" are interchangeable and refer to a molecule or group of atoms positioned between two moieties. A linker or spacer may be formed using a molecule that is differentially functionalized or activated with groups at either end to allow selective sequential reaction with the hapten and the carrier, but the same reactive moiety may also be used at both ends. For example, a hapten-protein conjugate may include a linker between the hapten and the polypeptide or peptide. Typically, linkers are bifunctional, meaning that the linker includes a functional group at each end, where the functional groups are used to couple the linker to the two moieties. The two functional groups may be the same (i.e., a homo-bifunctional linker) or different (i.e., a heterobifunctional linker). The groups selected for reaction with the hapten and the functional linking group to be bound to the carrier are determined by the type of functionality on the hapten and the carrier to which the hapten is to be bonded.

Any suitable carrier having immunogenic properties can be used, and conventional conditions for the coupling reaction can be employed. Immunogenic carriers are often proteins, but carriers can also include a sugar or fat in mono- or polymer form. In exemplary embodiments, the carrier molecule is streptavidin. The binding of the hapten to the carrier protein is often covalent, but it can be ionic or be effected through a chemical component bridging the hapten and the carrier. Under certain conditions it is possible to crosslink the hapten and no carrier substance is needed in order to make it immunogenic.

In some cases, the carrier protein is a member of a "specific binding pair," meaning two different molecules wherein one of the molecules, through chemical or physical means, specifically binds to the second molecule. In addition to antigen and antibody specific binding pairs, other specific binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like.

Any appropriate technique can be used to detect and measure the degree of conjugation of a nicotine hapten to an immunogenic carrier. For example, conjugation of a nicotine hapten to a polypeptide carrier can be estimated using a technique such as a protein assay or ultraviolet (UV) spectral analysis.

Any appropriate technique can be used to confirm the chemical structure of a nicotine hapten obtained according to the methods provided herein. For example, the chemical structure of a nicotine hapten can be confirmed by mass spectrometry, $^1$H-NMR spectrometry, or $^{13}$C spectrometry.

In another aspect, provided herein is a method of eliciting an immune response against a small molecule in a subject. The method comprises or consists essentially of administering to a subject in need thereof a composition comprises a nicotine hapten, thereby eliciting an immune response in the subject. In some cases, nicotine antibody-producing cells are isolated from an immunized subject, immortalized, and screened for the production of monoclonal antibodies. These monoclonal antibodies may, if desired, be prepared recombinantly by isolating the nucleic acids encoding them from the antibody-producing cells and manipulating the nucleic acids for recombinant production. Accordingly, modified forms of the antibodies, such as single-chain or Fv antibodies may be produced.

In a further aspect, provided herein is a method of producing antibodies to a nicotine hapten conjugate. The method comprises administering to an animal an effective amount of a nicotine hapten conjugate provided herein; isolating antibodies from sera of the animal; and recovering the isolated antibodies. Antibodies produced according to the method are anti-nicotine antibodies having specificity for the nicotine portion of the conjugate. In some cases, the antibody is a polyclonal antibody.

IV. Compositions

In another aspect, provided herein is an immunogenic conjugate comprising a nicotine hapten linked to a carrier molecule, where the conjugate elicits an immune response in a subject. Where the hapten is a drug of abuse or addiction such as nicotine, therapeutic compositions comprising hapten-carrier conjugates as described herein are particularly useful in the treatment of nicotine addiction. Such therapeutic compositions can be suitable for co-therapy with other conventional drugs. Passive immunization using antibodies raised against conjugates of the instant invention is also contemplated.

In a further aspect, provided herein are compositions comprising nicotine hapten conjugates as described herein and at least one other component, preferably at least one excipient or carrier and, most preferably, at least one pharmaceutically acceptable excipient or carrier. In exemplary embodiments, a composition of the invention comprises an immunogenic nicotine hapten conjugate and a pharmaceutically acceptable carrier.

The conjugates and compositions provided herein are useful for inducing immune responses against nicotine haptens and include nicotine vaccines. Such an anti-nicotine immune response can be utilized to generate antibodies, including those suitable for therapeutic, prophylactic, and diagnostic purposes. An anti-nicotine immune response can be useful to prevent or treat addiction to drugs of abuse and the resultant diseases associated with drug addiction.

As used herein, the term "vaccine" refers to a formulation which contains the composition of the present invention and which is in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition. Upon introduction into a host, the vaccine is able to provoke an immune response including, but not limited to, the production of antibodies and/or cytokines and/or the activation of cytotoxic T cells, antigen presenting cells, helper T cells, dendritic cells and/or cellular responses. Optionally, the vaccine of the present invention additionally includes an adjuvant which can be present in either a minor or major proportion relative to the compound of the present invention. Without being bound by any particular mechanism, it is believed that the use of a nicotine vaccine can induce a "memory" immune response upon exposure to nicotine and provide long-term anti-nicotine immunity.

As used herein, the term "antigen" refers to a compound, composition, or substance that may specifically bind the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins. As used herein, the term "epitope" refers to an antigenic determinant, meaning a particular chemical group or contiguous or non-contiguous peptide sequence on a molecule that elicits a specific immune response ("antigenic"). An antibody binds a particular antigenic epitope.

The term "antibody" is used herein in the broadest sense and specifically encompasses at least monoclonal antibodies, polyclonal antibodies, multi-specific antibodies (e.g., bispecific antibodies), chimeric antibodies, humanized antibodies, human antibodies, and antibody fragments. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes.

In some cases, a vaccine provided herein is administered with an adjuvant. As used herein, the term "adjuvant" refers to a compound or mixture of compounds that are added to or administered in conjunction with a vaccine in order to enhance antibody production efficacy or to help generate a specific class of antibodies as for example IgM immunoglobulins or antibodies able to bind complement. Substances suitable for use as an adjuvant include, without limitation, mineral oils, derivatives of aluminum, pathogen-associated molecular patterns (PAMPs) (e.g., lipopolysaccharide (LPS), porins, bacterial lipoproteins and lipopeptides, peptidoglycan, lipoteichoic acids, mannose-rich glycans, flagellin, bacterial and viral genomes, mycolic acid, and lipoarabinomannan), pattern-recognition receptors (PRRs), and danger-associated molecular patterns (DAMPs) such as microbial DNA and RNA or heat-shock proteins. Vaccines provided herein can be administered with or without an adjuvant.

Any appropriate mode of vaccine administration can be used. In some cases, for example, a vaccine described herein is intended for parenteral, topical, oral, or local administration. Preferably, the pharmaceutical compositions are administered parenterally, e.g., intravenously ("i.v."), subcutaneously ("s.c."), intradermally, or intramuscularly, however other modes of administration may be devised. Thus, provided herein are compositions for parenteral administration that comprise a solution of the nicotine hapten conjugates described above dissolved or suspended in a pharmaceutically acceptable carrier, preferably an aqueous carrier. A variety of pharmaceutically acceptable aqueous carriers may be used including, without limitation, water, buffered water, saline, glycine hyaluronic acid, and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain as pharmaceutically acceptable carriers, substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Nicotine hapten conjugates described herein are suitable for prophylactic uses as vaccines. For such uses, vaccines can be provided as a single administration or in two or more administrations or boosters.

Although the embodiments are described in considerable detail with reference to certain methods and materials, one skilled in the art will appreciate that the disclosure herein can be practiced by other than the described embodiments, which have been presented for purposes of illustration and not of limitation. Therefore, the scope of the appended claims should not be limited to the description of the embodiments contained herein.

EXAMPLES

Example 1—Rationale for Using Nic-Streptavidin Platform for Hapten Design

To rationally design the nicotine vaccines, we selected streptavidin (SA) as a protein carrier, owing to the following properties: 1) well-characterized crystal structure and known residues for nicotine conjugation, which allows both molecular modeling and experimental assessment of nicotine-streptavidin conjugates for examining their accessibility to nicotine-specific antibodies; 2) highly immunogenic nature; and 3) feasibility to make antigen-adjuvant complexes for enhanced immunity. With limited number of lysine residues for conjugation, the neighboring effect of conjugation sites can be modeled and assessed. On the other hand, also attributing to the same feature, the linker in the context of few conjugation sites per protein sites may constitute strong immunogenic epitopes to deter the immune reactions that are specific to free nicotine. Nevertheless, appropriate Nic-haptens, e.g., those with minimal linker effects upon conjugation to SA, could focus the immunity solely toward nicotine, which is the ultimate objective of this study. In our previous study, we categorized haptens according to their linker effect, which was calculated from their interactions with monoclonal anti-Nic antibody (5F3) and normalized against the binding activity of 5F3 to free nicotine.

One possibility is that a strong linker effect may constitute an epitope independent of the Nic moiety and interfere with immunity specific to the Nic moiety. Another possibility is that some linker-mediated effects may also exert a positive influence in the interaction between Nic-specific B cells and the Nic moiety, such as recruiting or promoting Nic-specific B cells to engage with Nic moiety.

Nicotine haptens of different lengths and chemical properties are expected to be highly variable in terms of conjugation efficiency, surface display, and linker effects on neighboring Nic moieties. Thus, it would be difficult or impossible to screen all variables in an animal model to identify those specific to Nic moiety. Instead, we combined the computational modeling approach with accessibility analysis based on competition ELISA to screen nicotine-streptavidin conjugates. The identified candidates were further tested for their immunogenicity and functionality.

To examine how newly synthesized nicotine interacts with nicotine-specific B cells, we used a nicotine-specific monoclonal antibody (5F3, with binding $K_d$ at 66 nM) to test its binding to these haptens. We argued that if the haptens displayed worse binding activity to the antibody than free nicotine, they would have structural disadvantage in competing for the interaction with nicotine-specific B cells, therefore these haptens would not be good vaccine candidates. On the other hand, many nicotine-specific antibodies bind better to their cognate nicotine haptens than free nicotine, in part attributed to the interaction of Fab conjugated to the linker region of the hapten. Although the linker effect may help secure the interaction with nicotine-specific B cells the dependence on the linker effect for attracting these B cells may also result in the recruitment of B cells with low intrinsic affinity in binding to free nicotine. Thus, we expected that the ideal haptens should exhibit antibody-binding affinity at the level close to the one seen with free nicotine. Thus, using competition ELISAs, we determined the binding activity of various haptens to 5F3 (expressed as $IC_{50\ HP}$), and normalized by the $IC_{50}$ of free nicotine to express as relative affinity index ($IC_{50HP}/IC_{50Nic}$). The higher the number reflects the lower the relative affinity. As summarized in FIG. 12, several haptens have the relative affinity larger than 1, indicating their worse binding to 5F3 than the one seen with free nicotine. In contrast, hapten 52, 45 and 138 show very high relative binding affinity (with the index less than 0.01). We suspect that the binding of these haptens to 5F3 is likely driven by the linker effect, which ultimately may compromise the selection for high-affinity nicotine-specific B cells. Thus, based on this analysis, haptens with intermediate binding affinity, i.e., their affinity index smaller than 1, but larger than 0.02, was considered as good hapten candidate as they have a balanced influence of the linker effect.

In order to assess the accessibility of free Nic moiety in the context of SA, we conducted molecular modeling, which eventually provided some insights about how well these nicotine haptens can be presented for antibody interactions. Given the well-characterized three-dimensional structure of SA, four lysine residues on the surface of SA are primary sites for Nic conjugation, i.e., K80, K121, K132 and K134.

We attempted to predict the binding affinity and conformation of different Nic haptens to SA using a rigid docking algorithm in the AutoDock4 program. In general, the binding conformation with the lowest energy is indicative of the better binding conformation of the ligand towards the receptor protein that has stronger binding affinity through interaction with ligands via neighboring amino acids. In the case of Nic haptens, the Nic moiety of the hapten should be stood out from the surface of the SA as much as possible in order to be available to interact with the anti-Nic antibody, and Nic-specific B cells. Here, we speculate that the conformation of Nic hapten having higher binding affinity to SA might result in reducing the availability of Nic moiety for antibody interaction. In other words, SA amino acids surrounding the Nic hapten influences the anti-Nic antibody interactions by making it least available. Therefore, we predicted that a good Nic hapten which elicits focused immunogenicity to the free Nic moiety should exhibit high binding energy.

We compared the binding energy of Nic haptens to four lysine positions in SA and analyzed their docking conformations. The conformations and interactions of different Nic haptens exhibited different behavior in these four lysine regions of SA. The streptavidin-hapten conjugation is expected to be between the reactive group at the linker end of the Nic hapten and the lysine side chain of the streptavidin. The docking of Nic hapten on to the streptavidin resulted in different conformations and orientations of Nic hapten near the exposed lysine residue along with the presence of expected conjugatable conformation. This is obvious due to the limitation that this docking algorithm cannot be able to precisely form the expected covalent conjugation reaction between the Nic hapten and streptavidin as is done experimentally. Rather than merely looking at the lowest energy conformation of Nic hapten, we analyzed for the presence of Nic hapten conformations having the linker end close to the lysine side chain with an interactable distance of 1.5 to 2.5 Å which may resemble the expected conjugation. For some Nic haptens at some lysine positions, our docking analysis did not predict these kind of expected conjugation which might be due to the influence of neighboring amino acids interactions that are incompatible with the Nic hapten at this kind of particular conformation. For the computational screening, selection and validation of Nic haptens, we utilized the binding energy parameter which reflect the affinity of these Nic haptens towards streptavidin. And for the comparison, we averaged the binding energy of Nic hapten at all four lysine positions for each Nic hapten.

First, we compared the lowest binding energy conformation of Nic haptens towards streptavidin irrespective of the presence of conformations with expected conjugation. This comparison may reflect the influence of neighboring amino acids of lysine in streptavidin to Nic haptens. The Nic haptens having lower binding energy may be worse than other Nic haptens because they interact strongly with streptavidin which may affect the antibody interaction. Second, we compared the binding energy of those which showed the expected conjugatable conformation of Nic hapten on to streptavidin. The Nic haptens having higher binding energy with this conjugatable conformation are considered good since they satisfy two expected criteria: one is having low binding affinity due to the higher binding energy and secondly, possessing the conformation compatible for conjugation. Since, some Nic haptens failed to show any expected conjugatable conformation at one or more lysine positions, they are also regarded as worse than those having expected conjugatable conformation at all four lysine positions.

Using competition ELISA, we examined the binding activity of Nic-specific mAb (5F3) to conjugated nicotine, in comparison to the one interacting with haptens alone. Based on the number of lysine residues per SA monomer, 16 lysine residues displayed on the surface of SA participate in conjugation to nicotine haptens. Thus, the fold of increase in binding activity from haptens to hapten-SA conjugates should only reach to 16. However, the competition ELISA data shows that the estimated affinity is much higher than 16, ranging from 30 to >500. These data suggest that the inclusion of streptavidin, especially local residues surrounding conjugated nicotine haptens, increases the overall binding of hapten-SA conjugates to 5F3.

If the interaction between 5F3 and Nic-SA somehow fixes the nicotine moiety in a certain conformation that resembles free nicotine in aqueous phase, the interaction should increase the efficacy of anti-Nic antibody responses. However, it is possible that the interactions produces a "linker effect" in which the linker is highly immunogenic and cause an increased antibody response toward the linker rather than free nicotine.

Considering these two possible scenarios, we reasoned that the effect of SA on the interaction between nicotine haptens and 5F3 should be at an intermediate level, where the SA linkage increases anti-Nic antibody responses with minimal linker-specific immunogenicity. Thus, computer-assisted modeling was combined with competition ELISA to identify haptens having intermediate indexes. We selected 140-hapten ("VA-II-140") as the best candidate. See FIG. 1. To validate our selection, 140-hapten along with the previously described nicotine hapten (1'Nic), 137 (which binds poorly to mAb), and 138 (which has a strong linker effect) were conjugated to SA for immunogenicity assays.

Balb/c mice were immunized with nicotine-SA conjugates three times, and serum was collected from each mouse after the 2nd and 3rd immunizations. As shown in FIG. 10, after three rounds of immunization, the level of anti-nicotine antibodies were significantly increased in mice immunized with 138-SA, 140-SA, whereas the anti-nicotine antibodies levels were rather low in mice immunized with 1'-Nic-SA and 137-SA. We also analyzed the relative binding affinity of elicited anti-nicotine antibodies for both free nicotine and their cognate haptens. Interestingly, for the antibody made in 138-immunized mice, although $IC_{50}HP$ are relatively low, the $IC_{50}$ to free nicotine is quite high, indicating their low affinity.

Figure 14:
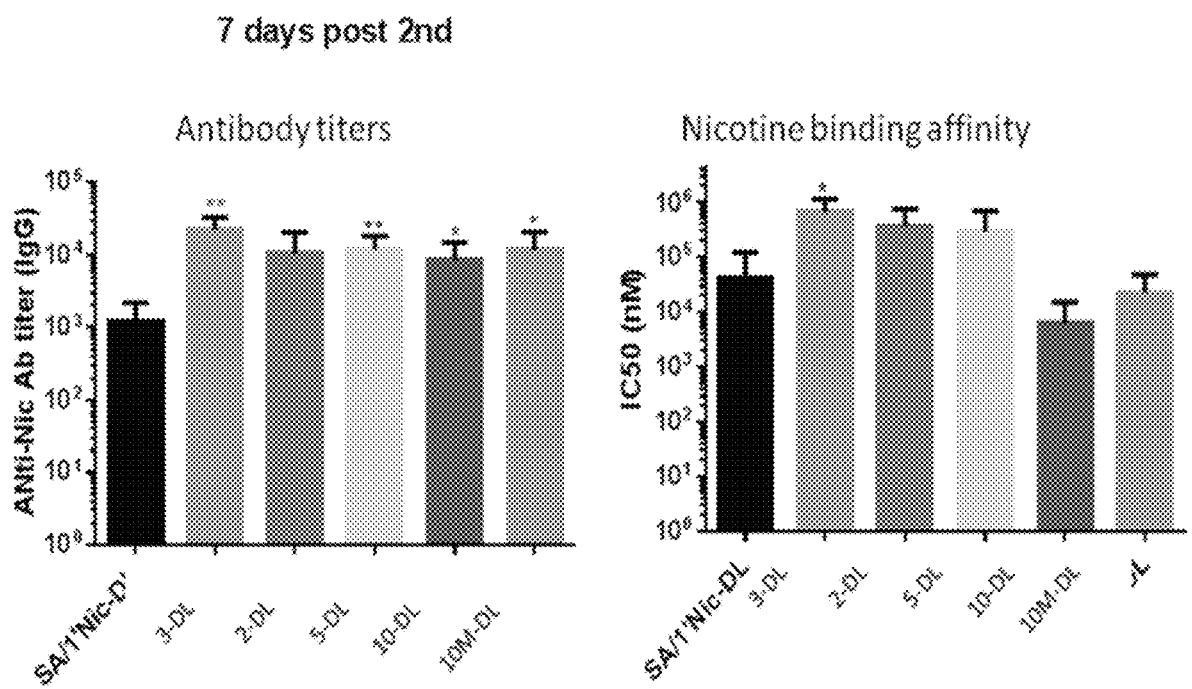
FIG. 14 demonstrates in vitro immunogenicity of selected haptens. Immunogenic responses induced by 10-DL (also known as 140) and 10M-DL (also known as 140M) exhibit have a high quality index (Ab-titer/$IC_{50}$) (i.e., a high quality response (high titer and high affinity)).

Small scale analysis was repeated for the same haptens. Hapten 140 and 140M (also referred to as 10 and 10M in, for example, FIG. 14) again exhibited induction of high quality antibody responses as determined by high titer and high affinity (low $IC_{50}$).

Materials and Methods

Products were concentrated by rotary evaporation (vacuum pump, ca. 7.5-25 Torr). Analytical thin-layer chromatography was performed using glass plates pre-coated with silica gel (0.25 mm, 60 Å pore size, 230-400 mesh, Silicycle) impregnated with a fluorescent indicator (254 nm). TLC plates were visualized by exposure to ultraviolet light (UV). Flash-column chromatography was performed employing silica gel (60 Å pore size, 40-63 μm, standard grade, Silicycle).

$^1$H NMR spectra was recorded on a Varian INOVA 400 (400 MHz) spectrometer at 25° C. Proton chemical shifts are expressed in parts per million (ppm, δ scale) and are referenced to residual protium in the NMR solvent (chloroform-d). Data are represented as follows: chemical shift, multiplicity (s=singlet, d=doublet, t=triplet, q=quartet, m=multiplet, brs=broad singlet), coupling constant (J) in Hertz (Hz) and integration.

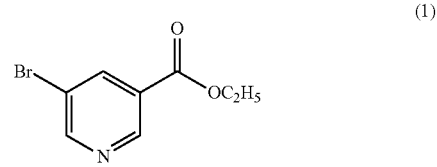 [SMILES: CCOC(=O)c1cncc(Br)c1]

Ethyl 5-bromonicotinate (1)

To an ice-cool solution of 5-bromonicotinic acid (15 g, 75 mmol) in ethanol (250 mL) was added concentrated sulfuric acid (4 mL) slowly drop wise and refluxed under argon for 18 h. Ethanol was removed under reduced pressure and resulting white residue was dissolved in water. The aqueous solution was made basic to pH 8 with sat. sodium bicarbonate and extracted with ether. The organic layer was washed with brine, dried over anhydrous $MgSO_4$, and concentrated under diminished pressure afforded 1 as a pale yellow solid: yield 15.20 g (89%); $^1$H NMR (400 MHz, $CDCl_3$) δ 1.39 (t, 3H, J=7.2 Hz), 4.40 (q, 2H, J=7.6, 14.8 Hz), 8.40 (t, 1H, J=2.0 Hz), 8.81 (d, 1H, J=2.4 Hz) and 9.10 (d, 1H, J=1.6 Hz); $^{13}$C NMR (100 MHz, $CDCl_3$) δ 14.3, 62.0, 120.7, 127.6, 139.5, 149.0, 154.5 and 164.1.

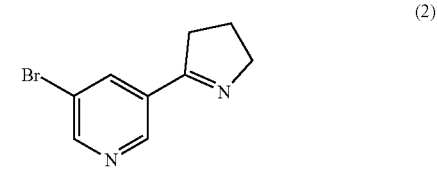 [SMILES: Brc1cncc(C2=NCCC2)c1]

3-Bromo-5-(4, 5-dihydro-3H-pyrrol-2-yl)-pyridine (2)

Sodium hydride (3.44 g, 86 mmol, 60% dispersion in oil) in a three-neck flask was washed with three 20 mL portions of hexane. The flask was fitted with a reflux condenser, flushed with argon, and charged with THF (70 mL). A solution of 1 (10 g, 66.1 mmol) and 1-vinyl-2-pyrrolidinone (7.89 g, 71 mmol) in THF (15 mL) was added in one portion. The mixture was stirred and refluxed for 1 h and then cooled to room temperature. A solution of concentrated HCl (12 mL) in water (18 mL) was added, and the THF was removed on a rotary evaporator. Additional concentrated HCl (18 mL) and water (36 mL) were added, and the mixture was heated at reflux overnight. In an ice-cooled bath, the solution was made basic with concentrated aqueous NaOH, which resulted in precipitation of the crude product, and then it was extracted with $CH_2Cl_2$ (2×75 mL). The combined $CH_2Cl_2$ layer was washed with water, brine, dried over anhydrous $MgSO_4$ and concentrated under diminished pressure. The residue was purified by chromatography on a silica gel column (15×5 cm) eluting with 19:1 $CH_2Cl_2$-acetone afforded 2 as a pale yellow solid: yield 6.87 g (70%); $^1$H NMR (400 MHz, $CDCl_3$) δ 2.00-2.08 (m, 2H), 2.86-2.92 (m, 2H), 4.02-4.08 (m, 2H), 8.31 (t, 1H, J=1.6 Hz), 8.67 (d, 1H, J=2.0 Hz) and 8.83 (d, 1H, J=1.6 Hz); $^{13}$C NMR (100 MHz, CDCl$_3$) δ 22.6, 34.9, 61.8, 121.0, 131.7, 137.2, 147.1, 152.2 and 169.9.

trile yielded 1.20 g (51%) of colorless needles [(S)-5-bromonornicotine (+)-MTPA salt].

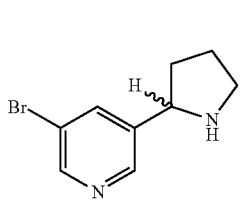

(3)

3-Bromo-5-(2-pyrrolidinyl)-pyridine (3)

A solution of compound 2 (2.0 g, 8.8 mmol) in 80 mL of 80:20 methanol/acetic acid was cooled at −40° C. with dry ice-acetonitrile bath. To this reaction mixture sodium borohydride (747 mg, 19.75 mmol) was added portion wise over 10 min with vigorous stirring. During the course of the addition, the temperature rose to −20° C. After warming to room temperature, most of the solvent was removed with a rotary evaporator. Water (200 mL) was added and the solution was made basic with NaOH and extracted with DCM (2×90 mL). The combined extracts were washed with brine, dried over K$_2$CO$_3$, and evaporated. The residue was purified by flash chromatography on a silica gel column (10×4 cm) eluting with 1:1 ethyl acetate-methanol afforded racemic 3 as a yellow oil: yield 1.8 g (90%); $^1$H NMR (400 MHz, CDCl$_3$) δ 1.56-1.66 (m, 1H), 1.81-1.95 (m, 3H), 2.16-2.25 (m, 1H), 3.00-3.06 (m, 1H), 3.11-3.17 (m, 1H), 4.15 (t, 1H, J=7.6 Hz), 7.88 (t, 1H, J=1.6 Hz), 8.46 (d, 1H, J=2.0 Hz) and 8.50 (d, 1H, J=2.4 Hz); $^{13}$C NMR (100 MHz, CDCl$_3$) δ 25.6, 34.7, 47.1, 59.3, 120.9, 136.8, 142.9, 146.8 and 149.2.

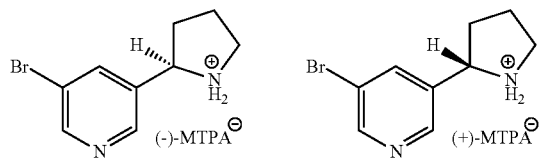 [SMILES: Brc1cncc([C@H]2CCCN2)c1 ; Brc1cncc([C@@H]2CCCN2)c1]

Resolution of Racemic 5-Bromonornicotine

To a solution compound 3 (2.33 g, 10.3 mmol) in ethyl acetate (16 mL) was added a solution of (−)-MTPA (1.2 g, 5.15 mmol) in ethyl acetate (4 mL) with stirring. The mixture was allowed to stand at room temperature for 15 min, after which time the crystalline product was collected by filtration to give (R)-isomer enriched crystals. Three recrystallizations from boiling acetonitrile yielded 1.28 g (54%) of colorless needles [(R)-5-bromonornicotine (−)-MTPA salt]. The filtrate was extracted with 1 N sulfuric acid (2×15 mL). The acid extracts were combined, washed with ether, made basic with NaOH, and extracted with DCM. The organic layer was evaporated to give an (S)-isomer enriched oil. The oil was dissolved in ethyl acetate (9 mL) and treated with a solution of (+)-MTPA (1.2 g, 5.15 mmol) in ethyl acetate (4 mL) with stirring. After the solution was left standing for 15 min, the crystallized product was collected by filtration. Three recrystallizations from boiling acetoni-

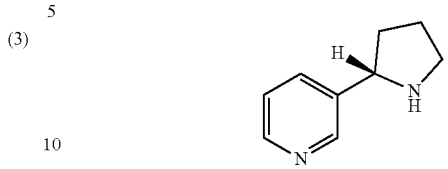

(S)-Nornicotine (5)

A suspension of (S)-5-bromonornicotine (+)-MTPA salt (500 mg, 1.08 mmol) in ether (80 mL) was vigorously shaken with 1 M KOH (30 mL) in a separating funnel. The ether layer was washed with 1 M KOH (30 mL), dried over anhydrous K$_2$CO$_3$, and evaporated. The residual oil was dissolved in ethanol (30 mL) containing Et$_3$N (0.6 mL) and hydrogen gas was babbled through the reaction mixture with 10% Pd/C (200 mg). After 1 h, the mixture was filtered through celite and the filter cake washed with ethanol. The filtrate was poured into 1 M K$_2$CO$_3$ (90 mL) which was then extracted with CH$_2$Cl$_2$ (2×100 mL). After washing with brine (50 mL), the combined extracts were dried over anhydrous K$_2$CO$_3$ and concentrated under diminished pressure. The residue was purified by flash chromatography on a silica gel column (10×1 cm) eluting with 7:1 CH$_2$Cl$_2$-methanol afforded 5 as a pale yellow oil; yield 85 mg (53%); $^1$HNMR (400 MHz, CDCl$_3$) δ 1.56-1.66 (m, 1H), 1.78-1.91 (m, 2H), 1.99 (brs, 1H), 2.11-2.20 (m, 1H), 2.96-3.02 (m, 1H), 3.11-3.17 (m, 1H), 4.10 (t, 1H, J=7.6 Hz), 7.17-7.20 (m, 1H), 7.64-7.67 (m, 1H), 8.42 (dd, 1H, J=1.6, 4.8 Hz) and 8.54 (d, 1H, J=2.0 Hz); $^{13}$C NMR (100 MHz, CDCl$_3$) δ 25.5, 34.4, 47.0, 60.1, 123.4, 134.1, 140.3, 148.3 and 148.6; MALDI-FTMS: 149 (MW).

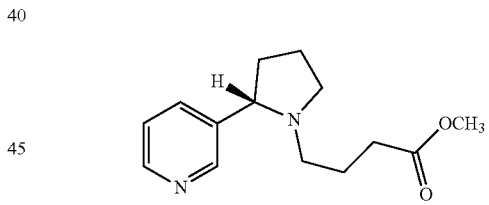

(S)-Methyl 4-(2-(pyridin-3-yl)pyrrolidin-1-yl)butanoate (6a)

A solution of methyl 4-iodobutanoate (227 mg, 1.21 mmol) in acetonitrile (0.4 mL) was added to a stirred solution of 5 (150 mg, 1.01 mmol) and diisopropylethylamine (0.53 mL, 3.03 mmol) in acetonitrile (0.8 mL) at room temperature. After 18 h, reaction mixture was concentrated under diminished pressure, residue was directly purified by flash chromatography on a silica gel column eluting (15×2 cm) with 5% methanol in CH$_2$Cl$_2$ afforded 6a as a pale yellow oil: yield 196 mg (78%); silica gel TLC R$_f$ 0.35 (5% methanol in CH$_2$Cl$_2$); $^1$H NMR (400 MHz, CDCl$_3$) δ 1.55-1.62 (m, 1H), 1.63-1.89 (m, 4H), 2.04-2.19 (m, 4H), 2.25-2.35 (m, 1H), 2.38-2.43 (m, 1H), 3.19-3.30 (m, 2H), 3.52 (s, 3H), 7.18 (dd, 1H, J=4.8, 7.6 Hz), 7.62 (d, 1H, J=8.0 Hz), 8.42 (s, 1H) and 8.47 (s, 1H); $^{13}$C NMR (100 MHz, CDCl$_3$) δ 22.7, 23.9, 31.7, 35.2, 51.4, 53.1, 53.2, 67.5, 123.5, 134.9, 139.6, 148.5, 149.5 and 174.0; Mass spectrum (APCI+), m/z 249.1606 (M+H)$^+$ (C$_{14}$H$_{21}$N$_2$O$_2$ requires m/z 249.1603).

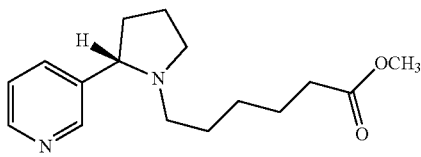

(S)-Methyl 6-(2-(pyridin-3-yl)pyrrolidin-1-yl)hexanoate (6b)

A solution of methyl 6-iodohexanoate (142 mg, 0.56 mmol) in acetonitrile (0.3 mL) was added to a stirred solution of 6 (75 mg, 0.51 mmol) and diisopropylethylamine (0.26 mL, 1.53 mmol) in acetonitrile (0.8 mL) at room temperature. After 18 h, reaction mixture was concentrated under diminished pressure, residue was directly purified by flash chromatography on a silica gel column (15×2 cm) eluting with 3% methanol in CH$_2$Cl$_2$ afforded 6b as a pale yellow oil: yield 106 mg, (75%); silica gel TLC R$_f$ 0.35 (5% methanol in CH$_2$Cl$_2$); $^1$H NMR (400 MHz, CDCl$_3$) δ 1.18-1.36 (m, 2H), 1.38-1.46 (m, 2H), 1.50-1.58 (m, 2H), 1.60-1.69 (m, 1H), 1.78-1.88 (m, 1H), 1.89-2.00 (m, 1H), 2.02-2.09 (m, 1H), 2.14-2.27 (m, 4H), 2.42-2.49 (m, 1H), 3.24 (t, 1H, J=8.0 Hz), 3.30-3.35 (m, 1H), 3.64 (s, 3H), 7.22-7.25 (dd, 1H, J=4.8, 8.0 Hz), 7.67-7.70 (m, 1H), 8.48 (d, 1H, J=3.6 Hz) and 8.54 (s, 1H); $^{13}$C NMR (100 MHz, CDCl$_3$) δ 22.6, 24.8, 26.9, 28.4, 34.0, 35.2, 51.4, 53.6, 54.2, 67.7, 123.5, 134.9, 139.7, 148.5, 149.5 and 174.1; Mass spectrum (APCI+), m/z 277.1925 (M+H)$^+$ (C$_{16}$H$_{25}$N$_2$O$_2$ requires m/z 277.1916).

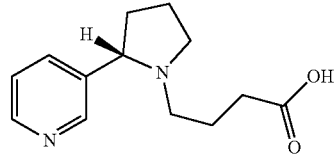

(S)-4-(2-(Pyridin-3-yl)pyrrolidin-1-yl)butanoic acid (7a)

A solution of 6a (63 mg, 0.25 mmol) in methanol (1 mL) was added aq NaOH (30 mg, 0.76 mmol) with stirring at room temperature. After 18 h, the reaction mixture was evaporated, dissolved in 2 mL of acetone and the pH was adjusted to 7 by using acetic acid. Acetone was evaporated and the crude product was directly purified by flash chromatography on a silica gel column (10×2 cm), eluting with 1:1.5 methanol-CH$_2$Cl$_2$ afforded 7a as a pale yellow oil: yield 38 mg (64%); silica gel TLC R$_f$ 0.3 (1:1.5 methanol-CH$_2$Cl$_2$); $^1$H NMR (400 MHz, CDCl$_3$) δ 1.70-1.80 (m, 3H), 1.82-2.08 (m, 2H), 2.17-2.29 (m, 2H), 2.30-2.42 (m, 2H), 2.54-2.61 (m, 1H), 3.44-3.51 (m, 3H), 7.32 (d, 1H, J=5.6 Hz), 7.84 (d, 1H, J=8.0 Hz), 8.50 (s, 1H), 8.55 (s, 1H) and 11.30 (brs, 1H); $^{13}$C NMR (100 MHz, CDCl$_3$) δ 22.4, 23.2, 33.8, 34.3, 53.3, 53.6, 67.7, 124.1, 135.9, 137.7, 148.3, 148.9 and 176.6; Mass spectrum (APCI+), m/z 235.1452 (M+H)$^+$ (C$_{13}$H$_{19}$N$_2$O$_2$ requires m/z 235.1447).

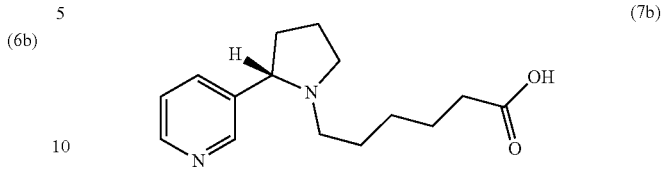

(S)-6-(2-(Pyridin-3-yl)pyrrolidin-1-yl)hexanoic acid (7b)

A solution of 6b (100 mg, 0.36 mmol) in methanol (0.6 mL) was added aq NaOH (44 mg, 1.09 mmol) with stirring at room temperature. After 18 h, the reaction mixture was evaporated, dissolved in 1 mL of acetone and the pH was adjusted to 7 by using acetic acid. Acetone was evaporated and the crude product was directly purified by flash chromatography on a silica gel column (10×2 cm), eluting with 1:1.5 methanol-CH$_2$Cl$_2$ afforded 7b as a pale yellow oil: yield 76 mg (80%); silica gel TLC R$_f$ 0.25 (1:1.5 methanol-CH$_2$Cl$_2$); $^1$H NMR (400 MHz, CDCl$_3$) δ 1.18-1.36 (m, 2H), 1.41-1.44 (m, 2H), 1.46-1.59 (m, 2H), 1.67-1.77 (m, 1H), 1.79-1.88 (m, 1H), 1.91-2.02 (m, 1H), 2.08-2.21 (m, 2H), 2.23-2.31 (m, 3H), 2.44-2.51 (m, 1H), 7.29 (d, 1H, J=7.2 Hz), 7.80 (d, 1H, J=7.6 Hz), 8.49 (d, 1H), 8.55 (s, 1H) and 13.51 (brs, 1H); $^{13}$C NMR (100 MHz, CDCl$_3$) δ 22.5, 25.0, 27.0, 28.0, 34.7, 34.8, 53.3, 54.1, 67.6, 123.9, 136.0, 139.2, 147.6, 148.5 and 177.6; Mass spectrum (APCI+), m/z 263.1761 (M+H)$^+$ (C$_{15}$H$_{23}$N$_2$O$_2$ requires m/z 263.1760).

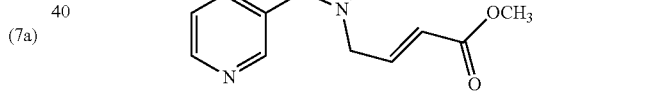

(S,E)-Methyl 4-(2-(pyridin-3-yl)pyrrolidin-1-yl)but-2-enoate (8)

A solution of (E)-methyl 4-iodobut-2-enoate (134 mg, 0.59 mmol) in acetonitrile (0.3 mL) was added to a stirred solution of 5 (80 mg, 0.54 mmol) and diisopropylethylamine (0.23 mL, 1.35 mmol) in acetonitrile (0.7 mL) at room temperature. After 18 h, reaction mixture was concentrated under diminished pressure, residue was directly purified by flash chromatography on a silica gel column (15×2 cm) eluting with 1:30 methanol-CH$_2$Cl$_2$ afforded 8 as a pale yellow oil (97 mg, 73%); silica gel TLC R$_f$ 0.45 (1:19 methanol-CH$_2$Cl$_2$); $^1$H NMR (400 MHz, CDCl$_3$) δ 1.57-1.66 (m, 1H), 1.73-1.80 (m, 1H), 1.84-1.90 (m, 1H), 2.01-2.16 (m, 2H), 2.17-2.24 (m, 1H), 2.99 (dd, 1H, J=6.8, 16.8 Hz), 3.64 (s, 3H), 5.90 (d, 1H, J=15.6 Hz), 6.79-6.86 (m, 1H), 7.17 (dd, 1H, J=4.8, 8.0 Hz), 7.62-7.65 (m, 1H), 8.41 (d, 1H, J=4.4 Hz) and 8.47 (d, J=2.0 Hz); $^{13}$C NMR (100 MHz, CDCl$_3$) δ 22.8, 35.1, 51.5, 53.8, 54.4, 66.79, 122.0, 123.7, 134.8, 138.8, 146.2, 148.8, 149.5 and 166.7; Mass spectrum (FAB+), m/z 247.1453 (M+H)$^+$ (C$_{14}$H$_{19}$N$_2$O$_3$ requires m/z 247.1447).

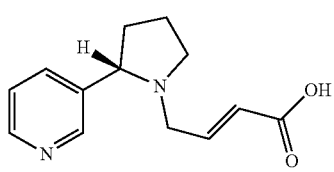

(9)

(S,E)-4-(2-(Pyridin-3-yl)pyrrolidin-1-yl)but-2-enoic acid (9)

A solution of 8 (95 mg, 0.39 mmol) in methanol (0.8 mL) was added aq NaOH (47 mg, 1.16 mmol) with stirring at room temperature. After 15 h, the reaction mixture was evaporated, dissolved in acetone (2 mL) and the pH was adjusted to 7 by using acetic acid. Acetone was evaporated and the crude product was directly purified by flash chromatography on a silica gel column (10×2 cm) eluting with 1:1.5 methanol-$CH_2Cl_2$ afforded 9 as a pale yellow oil (71 mg, 79%) as a pale yellow oil; silica gel TLC $R_f$ 0.4 (1:1.5 methanol-$CH_2Cl_2$); 1.64-1.76 (m, 1H), 1.79-1.88 (m, 1H), 1.90-2.02 (m, 1H), 2.18-2.26 (m, 1H), 2.29-2.36 (m, 1H), 2.93 (dd, 1H, J=6.4, 15.6 Hz), 3.33 (d, 1H, J=10.0 Hz), 3.48 (t, 1H, J=7.2 Hz), 6.00 (d, 1H, J=15.6 Hz), 6.88-6.95 (m, 1H), 7.32 (dd, 1H, J=4.8, 7.6 Hz), 7.82 (d, 1H, J=8.0 Hz), 8.51 (d, 1H, J=4.0 Hz), 8.58 (s, 1H) and 12.30 (brs, 1H); $^{13}C$ NMR (100 MHz, $CDCl_3$) δ 22.8, 35.0, 53.8, 54.4, 66.7, 123.6, 124.2, 136.1, 139.3, 145.8, 147.7, 148.4 and 169.9; Mass spectrum (FAB+), m/z 233.1286 $(M+H)^+$ ($C_{13}H_{17}N_2O_2$ requires m/z 233.1290).

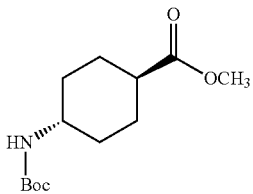

(11)

(1r,4r)-Methyl 4-((tert-butoxycarbonyl)amino)cyclohexanecarboxylate (11)

To a stirred solution of (1r,4r)-4-((tert-butoxycarbonyl)amino)cyclohexanecarboxylic acid (10, 150 mg, 0.617 mmol) in dry $CH_2Cl_2$ (5 mL) at 0° C. was added $Et_3N$ (0.17 mL, 1.234 mmol), after few minutes isopropylchloroformate (84 μL, 0.648 mmol) was added. After 1 h stirring at 0° C., excess amount of methanol (0.5 mL) was added to reaction mixture and allowed to warm to room temperature. After 15 hours, reaction mixture was concentrated under diminished pressure, residue was dissolved in $CH_2Cl_2$ (25 mL) and washed with sat. $NaHCO_3$ solution, brine, dried over anhydrous $MgSO_4$ and concentrated. The residue was purified by chromatography on silica gel column (15×2 cm) eluting with 4:1 hexane-ethyl acetate afforded 11 as a white solid: yield 147 mg (92%); silica gel TLC $R_f$ 0.6 (4:1 hexane-ethyl acetate); $^1H$ NMR (400 MHz, $CDCl_3$) δ 1.03-1.13 (m, 2H), 1.40 (s, 9H), 1.41-1.54 (m, 2H), 1.95-2.05 (m, 4H), 2.15-2.22 (m, 1H), 3.37 (brs, 1H), 3.63 (s, 3H) and 4.42 (brs, 1H); $^{13}C$ NMR (100 MHz, $CDCl_3$) δ 27.9, 28.5, 32.6, 42.4, 49.1, 51.7, 79.3, 155.2 and 175.9;

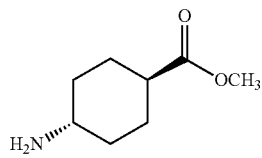

(12)

(1r,4r)-Methyl 4-aminocyclohexanecarboxylate (12)

To an ice-cool solution of 11 (140 mg, 0.54 mmol) in dry $CH_2Cl_2$ (2 mL) was added trifluoroacetic acid (0.62 mL, 8.17 mmol) with stirring. After 18 h at room temperature, reaction mixture was evaporated with toluene (1 mL×3 times) to give 12, which was directly used for the next reaction without any further purification.

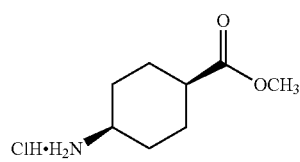

(14)

(1s,4s)-Methyl 4-aminocyclohexanecarboxylate hydrochloride (14)

To a solution of (1s,4s)-4-aminocyclohexanecarboxylic acid (13, 50 mg, 0.35 mmol) in methanol (2 mL) at 0° C. was added thionyl chloride (76 μL, 1.05 mmol) drop wise. After addition the reaction mixture was allowed to warm to room temperature and stirred for overnight. Reaction mixture was concentrated under diminished pressure yielded (1s,4s)-methyl 4-aminocyclohexanecarboxylate hydrochloride (14) as a white solid, which was directly used in next reaction.

(16)

(1R,3S)-Methyl 3-aminocyclopentanecarboxylate hydrochloride (16)

To a stirred solution of (1R,4S)-2-azabicyclo[2.2.1]hept-5-en-3-one (15, 100 mg, 0.91 mmol) in ethyl acetate (5 mL) was added 10% Pd/C (15 mg) and hydrogenated for 12 h by using hydrogen balloons at room temperature. Reaction mixture was filtered through celite bed, filter cake washed with ethyl acetate (3 mL). The combined organic layers was concentrated under reduced pressure afforded (1S,4R)-2-azabicyclo[2.2.1]heptan-3-one as a white solid, which directly used in the next reaction. To an ice-cool stirred solution of (1S,4R)-2-azabicyclo[2.2.1]heptan-3-one in methanol (3 mL) was added thionylchloride (0.2 mL, 1.64 mmol). After 24 h at room temperature, reaction mixture was concentrated under diminished pressure afforded 16 as a white solid: yield 109 mg (66%), which was directly used in the next reaction; $^1$H NMR (400 MHz, D$_2$O) δ 1.80-1.89 (m, 1H), 1.90-1.97 (m, 1H), 1.99-2.06 (m, 1H), 2.09-2.13 (m, 1H), 2.14-2.21 (m, 1H), 2.42-2.50 (m, 1H), 3.03-3.11 (m, 1H) and 3.76-3.82 (m, 4H (3+1)), $^{13}$C NMR (100 MHz, D$_2$O) δ 27.4, 29.8, 33.6, 42.2, 51.4, 52.6 and 178.3.

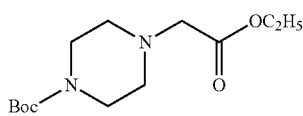

(17)

tert-Butyl 4-(2-ethoxy-2-oxoethyl)piperazine-1-carboxylate (18)

To a stirred solution of N-Boc piperazine (17, 300 mg, 1.61 mmol) in dry DMF (2 mL) was added K$_2$CO$_3$ and ethyl iodoacetate (345 mg, 1.61 mmol) at room temperature. After 15 h, the reaction mixture was diluted with water (25 mL), extracted with ethyl acetate (2×30 mL). The combined organic phase was washed with brine, dried over anhydrous MgSO$_4$ and concentrated under diminished pressure. The residue was purified by chromatography on a silica gel column (10×2 cm) eluting with 1:1 ethyl acetate-hexanes yielded 18 as a pale yellow oil: yield 320 mg (73%); silica gel TLC R$_f$ 0.51 (1:1 ethyl acetate-hexanes); $^1$H NMR (400 MHz, CDCl$_3$) δ 1.28 (t, 3H, J=7.2 Hz), 1.46 (s, 9H), 2.54 (t, 4H, J=4.8 Hz), 3.23 (s, 2H), 3.48 (t, 4H, J=4.8 Hz), and 4.19 (q, 2H, J=7.2, 12.0 Hz); $^{13}$C NMR (100 MHz, CDCl$_3$) δ 14.3, 28.5, 52.8, 59.5, 60.7, 79.7, 154.7 and 170.2.

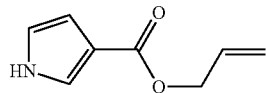

(21)

Allyl 1H-pyrrole-3-carboxylate (21)

To a solution of 1H-pyrrole-3-carboxylic acid (20, 160 mg, 1.44 mmol) in methanol (5 mL) was added Cs$_2$CO$_3$ (470 mg, 1.44 mmol) and stirred for 10 min at room temperature. The reaction mixture was concentrated under diminished pressure and the residue was re-dissolved in DMF (20 mL). To this, allyl bromide (0.37 mL, 4.32 mmol) was added and stirred for 1 h at room temperature. The reaction mixture was poured in water (50 mL), extracted with ethyl acetate (2×20 mL). The combined organic phase was washed with aq saturated NaHCO$_3$, water, brine and concentrated under diminished pressure. The residue was purified by chromatography on a silica gel column (20×2 cm) eluting 1:4 ethyl acetate-hexanes afforded 21 as a pale yellow liquid: yield 145 mg (67%); silica gel TLC R$_f$ 0.62 (1:4 ethyl acetate-hexanes); $^1$H NMR (400 MHz, CDCl$_3$) δ 4.73-4.75 (m, 2H), 5.22-5.25 (dd, 1H, J=1.2, 10.4 Hz), 5.34-5.38 (dd, 1H, J=1.6, 17.2 Hz), 5.95-6.05 (m, 1H), 6.64-6.66 (dd, 1H, J=2.8, 4.0 Hz), 6.73-6.75 (dd, 1H, J=2.4, 4.8 Hz), 7.42-7.44 (m, 1H) and 9.47 (brs, 1H); $^{13}$C NMR (100 MHz, CDCl$_3$) δ 64.5, 109.6, 115.7, 117.6, 119.2, 124.0, 132.7 and 165.4; Mass spectrum (FAB+), m/z 152.0707 (M+H)$^+$ (C$_8$H$_{10}$NO$_2$ requires m/z 152.0712).

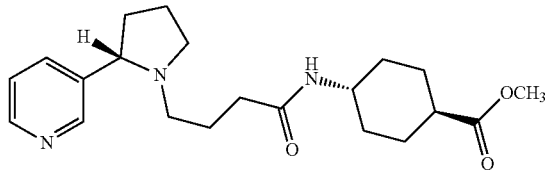

(22)

(1S,4r)-Methyl 4-(4-((S)-2-(pyridin-3-yl)pyrrolidin-1-yl)butanamido)cyclohexanecarboxyl-ate (22)

To a stirred solution of 7a (40 mg, 0.171 mmol) in dry DMF (0.7 mL) was added HBTU (71 mg, 0.188 mmol) at 0° C. After 10 min, a solution of 12 and N-methylmorpholine (55 μL, 0.512 mmol) in dry DMF (0.4 mL) was added at 0° C. After 18 h at room temperature, the reaction mixture was partitioned between ethyl acetate (25 mL) and water (20 mL). The aqueous layer was again extracted with ethyl acetate (20 mL), combined organic layers was washed with water, brine, dried over anhydrous MgSO$_4$ and concentrated under diminished pressure. The residue was purified by chromatography on a silica gel column (10×1 cm), eluting with 5% methanol-CH$_2$Cl$_2$ afforded 22 as a pale yellow oil: yield 21 mg (33%); silica gel TLC R$_f$ 0.31 (5% methanol-CH$_2$Cl$_2$); $^1$H NMR (400 MHz, CDCl$_3$) δ 1.45-1.57 (m, 2H), 1.68-1.81 (m, 3H), 1.88-2.01 (m, 6H), 2.06-2.36 (m, 8H), 3.37-3.46 (m, 2H), 3.63-3.75 (m, 3+1 H), 5.67-5.80 (d, 1H), 7.24-7.30 (m, 1H), 7.66-7.70 (m, 1H), 8.49 (d, 1H) and 8.56 (s, 1H); $^{13}$C NMR (100 MHz, CDCl$_3$) δ 22.6, 24.1, 27.5, 32.0, 34.6, 34.9, 42.3, 47.7, 51.6, 53.4, 53.7, 67.8, 123.7, 135.1, 148.7, 149.4, 172.3 and 175.7; Mass spectrum (APCI+), m/z 374.2437 (M+H)$^+$ (C$_{21}$H$_{32}$N$_3$O$_3$ requires m/z 374.2444).

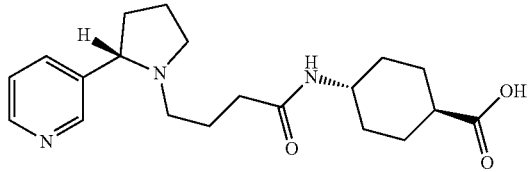

(23)

(1S,4r)-4-(4-((S)-2-(Pyridin-3-yl)pyrrolidin-1-yl)butanamido)cyclohexanecarboxylic acid (23)

A solution of 22 (21 mg, 0.056 mmol) in methanol (0.6 mL) was added aq NaOH (6 mg, 0.14 mmol) with stirring at room temperature. After 36 h, the reaction mixture was evaporated, dissolved in 1 mL of acetone and the pH was adjusted to 7 by using acetic acid. Acetone was evaporated and the crude product was directly purified by flash chromatography on a silica gel column (10×1 cm), eluting with 1:1.5 methanol-CH$_2$Cl$_2$ afforded 23 as a pale yellow oil: yield 12 mg (59%); silica gel TLC R$_f$ 0.25 (1:1.5 methanol-CH$_2$Cl$_2$); $^1$H NMR (400 MHz, CDCl$_3$) δ 0.99-1.17 (m, 2H), 1.50-1.60 (m, 2H), 1.66-1.81 (m, 3H), 1.83-1.93 (m, 2H), 1.94-2.06 (m, 4H), 2.09-2.15 (m, 1H), 2.17-2.30 (m, 5H), 2.42-2.49 (m, 1H), 3.34-3.43 (m, 2H), 3.62-3.77 (m, 1H), 6.11 (d, 1H, J=7.6 Hz), 7.31 (s, 1H), 7.73 (d, 1H, J=7.6 Hz), 8.48 (s, 1H), 8.68 (s, 1H) and 11.30 (brs, 1H); $^{13}$C NMR (100 MHz, CDCl$_3$) δ 22.6, 23.9, 28.04, 32.08, 34.19, 34.94, 47.64, 53.18, 53.55, 67.81, 123.71, 136.5, 139.2, 146.89, 148.09 and 172.16; Mass spectrum (APCI+), m/z 360.2282 (M+H)$^+$ (C$_{20}$H$_{30}$N$_3$O$_3$ requires m/z 360.2287).

(24)

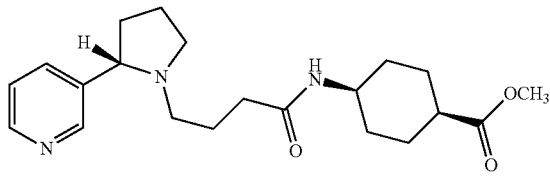

(1R,4s)-methyl 4-(4-((S)-2-(pyridin-3-yl)pyrrolidin-1-yl)butanamido)cyclohexanecarboxy-late (24)

To a stirred solution of 7a (38 mg, 0.162 mmol) in dry DMF (0.7 mL) was added HBTU (68 mg, 0.178 mmol) at 0° C. After 10 min, a solution of 14 and N-methylmorpholine (53 µL, 0.487 mmol) in dry DMF (0.4 mL) was added at 0° C. After 18 h at room temperature, reaction mixture was partitioned between ethyl acetate (25 mL) and water (20 mL). The aqueous layer was again extracted with ethyl acetate (20 mL), combined organic layers was washed with water, brine, dried over anhydrous MgSO$_4$ and concentrated under diminished pressure. The residue was purified by chromatography on a silica gel column (15×1 cm), eluting with 5% methanol-CH$_2$Cl$_2$ afforded 24 as a pale yellow oil: yield (22 mg, 36%); silica gel TLC R$_f$ 0.31 (5% methanol-CH$_2$Cl$_2$); $^1$H NMR (500 MHz, CDCl$_3$) δ 1.39-1.51 (m, 2H), 1.61-1.81 (m, 7H), 1.82-2.02 (m, 4H), 2.03-2.10 (m, 1H), 2.14-2.39 (m, 4H), 2.44-2.52 (m, 2H), 3.32-3.45 (m, 2H), 3.68 (s, 3H), 3.80-3.90 (m, 1H), 5.79-5.93 (brs, 1H), 7.25-7.31 (m, 1H), 7.69 (d, 1H), 8.49 (s, 1H), and 8.55 (s, 1H); $^{13}$C NMR (125 MHz, CDCl$_3$) δ 22.49, 24.20, 24.94, 29.03, 34.67, 39.69, 46.00, 51.57, 53.35, 53.77, 67.78, 123.51, 135.01, 148.64, 149.36, 172.15 and 175.38; Mass spectrum (APCI+), m/z 374.2443 (M+H)$^+$ (C$_{21}$H$_{32}$N$_3$O$_3$ requires m/z 374.2444).

(25)

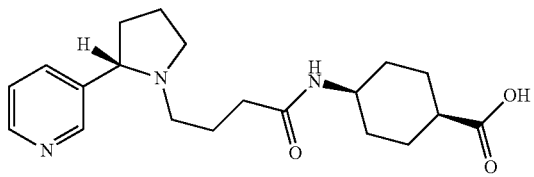

(1R,4s)-4-(4-((S)-2-(Pyridin-3-yl)pyrrolidin-1-yl)butanamido)cyclohexanecarboxylic acid (25)

A solution of 24 (22 mg, 0.059 mmol) in methanol (0.6 mL) was added aq NaOH (12 mg, 0.295 mmol) with stirring at room temperature. After 36 h, the reaction mixture was evaporated, dissolved in 1 mL of acetone and the pH was adjusted to 7 by using acetic acid. Acetone was evaporated and the crude product was directly purified by flash chromatography on a silica gel column (10×1 cm), eluting with 1:1.5 methanol-CH$_2$Cl$_2$ afforded 25 as a pale yellow oil: yield 11 mg (52%); silica gel TLC R$_f$ 0.25 (1:1.5 methanol-CH$_2$Cl$_2$); $^1$H NMR (400 MHz, CDCl$_3$) δ 1.32-1.39 (m, 1H), 1.42-1.51 (m, 3H), 1.63-1.72 (m, 4H), 1.74-1.88 (m, 3H), 1.91-2.05 (m, 3H), 2.11-2.29 (m, 5H), 2.40-2.54 (m, 2H), 5.62 (d, 1H), 7.24-7.35 (m, 1H), 7.64 (d, 1H), 8.46 (s, 1H), 8.75 (s, 1H), 10.64-11.45 (brs, 1H); $^{13}$C NMR (100 MHz, CDCl$_3$) δ 22.58, 23.76, 25.36, 29.49, 33.75, 34.85, 46.11, 53.41, 53.63, 67.93, 123.58, 136.71, 146.55, 147.97, 171.91; Mass spectrum (APCI+), m/z 360.2279 (M+H)$^+$ (C$_{20}$H$_{30}$N$_3$O$_3$ requires m/z 360.2287).

(26)

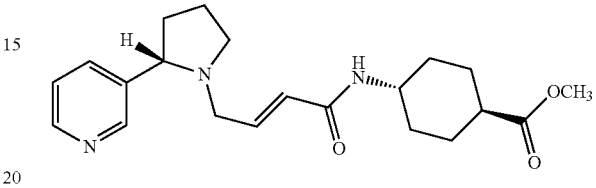

(1S,4r)-Methyl 4-((E)-4-((S)-2-(pyridin-3-yl)pyrrolidin-1-yl)but-2-enamido)cyclohexane-carboxylate (26)

To an ice-cool stirred solution of 9 (70 mg, 0.30 mmol) in dry DMF (0.9 mL) was added HATU (126 mg, 0.33 mmol). After 10 min, a solution of 12 and N-methylmorpholine (83 µL, 0.75 mmol) in dry DMF (0.4 mL) was added at 0° C. After 18 h at room temperature, the reaction mixture was diluted with water (20 mL), extracted with ethyl acetate (2×20 mL). The combined organic phase was washed with brine, dried over anhydrous MgSO$_4$ and concentrated under diminished pressure. The residue was purified by flash chromatography on a silica gel column (20×2 cm) eluting with 1:19 methanol-CH$_2$Cl$_2$ afforded 26 as a pale yellow oil: yield 67 mg (60%); silica gel TLC R$_f$ 0.3 (1:19 methanol-CH$_2$Cl$_2$); $^1$H NMR (400 MHz, CDCl$_3$) δ 1.07-1.15 (m, 2H), 1.35-1.40 (m, 2H), 1.43-1.52 (m, 2H), 1.56-1.65 (m, 1H), 1.74-1.97 (m, 6H), 2.00-2.26 (m, 3H), 2.77 (dd, 1H, J=7.2, 15.2 Hz), 3.12-3.25 (m, 2H), 3.33 (t, 1H, J=8.0 Hz), 3.59 (s, 3H), 3.64-3.77 (m, 1H), 5.67 (s, 1H, J=8.0 Hz), 5.83 (d, 1H, J=15.6 Hz), 6.61-6.69 (m, 1H), 7.19 (dd, 1H, J=8.0, 12.4 Hz), 7.64 (d, 1H, J=8.0 Hz), 8.40 (s, 1H) and 8.45 (s, 1H); $^{13}$C NMR (100 MHz, CDCl$_3$) δ 22.8, 27.8, 32.1, 35.1, 42.4, 47.8, 51.7, 53.8, 54.4, 66.7, 123.8, 125.2, 135.1, 139.1, 140.9, 148.6, 149.4, 164.9 and 175.8; Mass spectrum (FAB+), m/z 372.2286 (M+H)$^+$ (C$_{21}$H$_{30}$N$_3$O$_3$ requires m/z 372.2287).

(27)

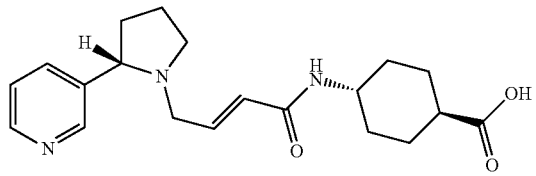

(1S,4r)-4-((E)-4-((S)-2-(Pyridin-3-yl)pyrrolidin-1-yl)but-2-enamido)cyclohexanecarboxylic acid (27)

A solution of 26 (67 mg, 0.18 mmol) in methanol (0.7 mL) was added aq NaOH (22 mg, 0.54 mmol) with stirring at room temperature. After 36 h, the reaction mixture was concentrated under diminished pressure, dissolved in acetone (3 mL) and the pH was adjusted to 7 by using acetic acid. Acetone was evaporated and the crude product was directly purified by flash chromatography on a silica gel column eluting (10×2 cm) with 1:1.5 methanol-CH$_2$Cl$_2$ afforded 27 as a colorless oil: yield 43 mg (67%); silica gel TLC R$_f$ 0.25 (1:1.5 methanol-CH$_2$Cl$_2$); $^1$H NMR (400 MHz, CD$_3$OD) δ 1.24 (q, 2H, J=11.6, 24.0 Hz), 1.42-1.53 (m, 2H), 1.65-1.75 (m, 1H), 1.83-2.00 (m, 6H), 2.14-2.29 (m, 2H), 2.38 (q, 1H, J=8.4, 18.0 Hz), 2.94 (dd, 1H, J=7.2, 16.4 Hz), 3.25-3.33 (m, 2H), 3.51 (t, 1H, J=8.4 Hz), 3.59-3.67 (m, 1H), 6.02 (d, 1H, J=15.2 Hz), 6.61-6.69 (m, 1H), 7.39 (t, 1H, J=7.6 Hz), 7.86 (d, 1H, J=8.0 Hz), 8.40 (d, 1H, J=3.6 Hz) and 8.49 (s, 1H); $^{13}$C NMR (100 MHz, CD$_3$OD) δ 23.7, 29.4, 32.9, 35.9, 44.1, 55.0, 55.7, 62.2, 125.6, 126.9, 137.7, 140.7, 141.4, 149.2, 149.8, 167.2 and 180.2; Mass spectrum (FAB+), m/z 358.2130 (M+H)$^+$ (C$_{20}$H$_{28}$N$_3$O$_3$ requires m/z 358.2131).

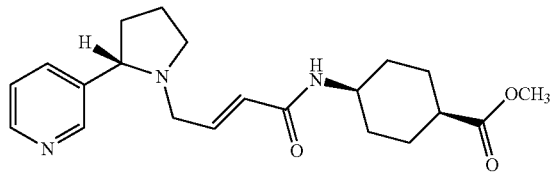

(1R,4s)-Methyl 4-((E)-4-((S)-2-(pyridin-3-yl)pyrrolidin-1-yl)but-2-enamido)cyclohexane-carboxylate (28)

To an ice-cool stirred solution of 9 (68 mg, 0.29 mmol) in dry DMF (0.7 mL) was added HBTU (123 mg, 0.32 mmol). After 10 min, a solution of 14 and N-methylmorpholine (97 µL, 0.88 mmol) in dry DMF (0.3 mL) was added at 0° C. After 18 h at room temperature, the reaction mixture was diluted with water (20 mL), extracted with ethyl acetate (2×20 mL). The combined organic phase was washed with brine, dried over anhydrous MgSO$_4$ and concentrated under diminished pressure. The residue was purified by flash chromatography on a silica gel column (20×2 cm), eluting with 1:19 methanol-CH$_2$Cl$_2$ afforded 28 as a pale yellow oil: yield 52 mg (48%); silica gel TLC R$_f$ 0.3 (1:19 methanol-CH$_2$Cl$_2$); $^1$H NMR (400 MHz, CDCl$_3$) δ 1.51-1.57 (m, 2H), 1.60-1.75 (m, 4H), 1.77-1.94 (m, 4H), 2.13-2.29 (m, 2H), 2.45-2.48 (m, 1H), 2.81 (dd, 1H, J=6.4, 15.6 Hz), 3.23-3.30 (m, 2H), 3.37 (t, 1H, J=8.0 Hz), 3.59-3.66 (m, 4H (3+1)), 3.93-3.97 (m, 1H), 5.60 (d, 1H, J=6.4 Hz), 5.88 (d, 1H, J=15.2 Hz), 6.66-6.73 (m, 1H), 7.23 (d, 1H, J=11.2 Hz), 7.68 (d, 1H, J=7.6 Hz), 8.45 (s, 1H) and 8.51 (s, 1H); $^{13}$C NMR (100 MHz, CDCl$_3$) δ 22.8, 25.1, 25.2, 29.4, 29.7, 35.1, 40.1, 46.0, 51.7, 53.8, 54.4, 66.8, 123.8, 125.2, 135.0, 139.0, 141.0, 148.8, 149.5, 164.9, 175.7; Mass spectrum (FAB+), m/z 372.2283 (M+H)$^+$ (C$_{21}$H$_{30}$N$_3$O$_3$ requires m/z 372.2287).

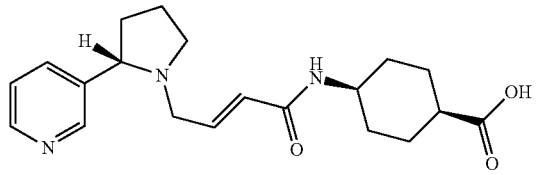

(1R,4s)-4-((E)-4-((S)-2-(Pyridin-3-yl)pyrrolidin-1-yl)but-2-enamido)cyclohexanecarboxylic acid (29)

A solution of 28 (50 mg, 0.14 mmol) in methanol (0.7 mL) was added aq NaOH (16 mg, 0.40 mmol) with stirring at room temperature. After 36 h, the reaction mixture was evaporated, dissolved in acetone (3 mL) and the pH was adjusted to 7 by using acetic acid. Acetone was evaporated and the residue was directly purified by flash chromatography on a silica gel column (10×2 cm) eluting with 1:1.5 methanol-CH$_2$Cl$_2$ afforded 29 as a colorless oil: yield 32 mg (67%); silica gel TLC R$_f$ 0.25 (1:1.5 methanol-CH$_2$Cl$_2$); $^1$H NMR (400 MHz, DMSO-d$_6$) δ 1.42-1.48 (m, 2H), 1.52-1.61 (m, 5H), 1.77-1.84 (m, 4H), 2.13-2.27 (m, 2H), 2.37 (s, 1H), 2.80 (dd, 1H, J=4.0, 16.0 Hz), 3.15-3.24 (m, 2H), 3.43 (t, 1H, J=7.6 Hz), 3.73 (d, 1H, J=3.6 Hz), 6.08 (d, 1H, J=15.2 Hz), 6.48-6.55 (m, 1H), 7.35 (dd, 1H, J=5.2, 8.0 Hz), 7.74 (d, 1H, J=8.0 Hz), 7.85 (d, 1H, J=7.2 Hz), 8.45 (s, 1H), 8.52 (s, 1H) and 12.10 (brs, 1H); $^{13}$C NMR (100 MHz, DMSO-d$_6$) δ 22.4, 24.6, 29.0, 34.7, 45.2, 48.6, 53.1, 53.9, 65.8, 123.7, 125.7, 134.7, 138.9, 139.0, 148.4, 148.9, 163.8 and 176.1; Mass spectrum (FAB+), m/z 358.2124 (M+H)$^+$ (C$_{20}$H$_{28}$N$_3$O$_3$ requires m/z 358.2131).

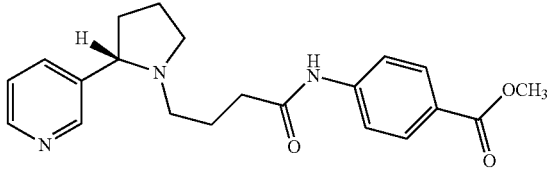

(S)-Methyl 4-(4-(2-(pyridin-3-yl)pyrrolidin-1-yl)butanamido)benzoate (30)

To an ice-cool stirred solution of 7a (48 mg, 0.205 mmol) in dry DMF (0.7 mL) was added HBTU (94 mg, 0.246 mmol). After 10 min, a solution of methyl 4-aminobenzoate (37 mg, 0.246 mmol) and N-methylmorpholine (68 µL, 0.615 mmol) in dry DMF (0.3 mL) was added at 0° C. After 18 h at room temperature, the reaction mixture was diluted with water (20 mL), extracted with ethyl acetate (2×20 mL). The combined organic phase was washed with brine, dried over anhydrous MgSO$_4$ and concentrated under diminished pressure. The residue was purified by chromatography on a silica gel column (15×2 cm), eluting with 1:19 methanol-CH$_2$Cl$_2$ afforded 30 as a pale yellow oil: yield 37 mg (49%); silica gel TLC R$_f$ 0.3 (1:19 methanol-CH$_2$Cl$_2$); $^1$H NMR (400 MHz, CDCl$_3$) δ 1.71-1.95 (m, 5H), 2.18-2.31 (m, 4H), 2.36-2.41 (m, 1H), 2.47-2.50 (m, 1H), 3.32-3.39 (m, 2H), 3.87 (s, 3H), 7.16 (t, 1H, J=3.6 Hz), 7.58 (t, 2H, J=3.6 Hz), 7.67 (s, 1H), 7.93-7.96 (m, 2H), 8.42 (s, 1H), 8.54 (s, 1H and 8.78 (s, 1H); $^{13}$C NMR (100 MHz, CDCl$_3$) δ 22.7, 24.0, 34.0, 35.7, 52.1, 53.5, 53.9, 68.1, 118.8, 123.8, 125.2, 130.8, 135.4, 142.8, 148.6, 149.4, 166.8 and 171.8; Mass spectrum (FAB+), m/z 368.1970 (M+H)$^+$ (C$_{21}$H$_{26}$N$_3$O$_3$ requires m/z 368.1974).

(31)

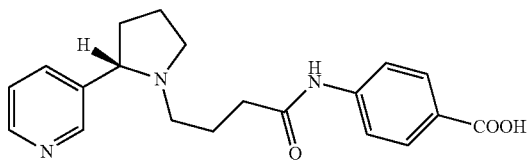

(S)-4-(4-(2-(Pyridin-3-yl)pyrrolidin-1-yl)butanamido)benzoic acid (31)

A solution of 30 (35 mg, 0.095 mmol) in methanol (0.5 mL) was added aq NaOH (12 mg, 0.286 mmol) with stirring at room temperature. After 18 h, the reaction mixture was evaporated, residue was dissolved in acetone (3 mL) and the pH was adjusted to 7 by using acetic acid. Acetone was evaporated under diminished pressure and the residue was directly purified by flash chromatography on a silica gel column (10×1 cm) eluting with 1:1.5 methanol-CH$_2$Cl$_2$ afforded 31 as a colorless oil (19 mg, 57%); silica gel TLC R$_f$ 0.22 (1:1.5 methanol-CH$_2$Cl$_2$); $^1$H NMR (400 MHz, DMSO-d$_6$) δ 1.54 (brs, 1H), 1.62-1.72 (m, 2H), 1.78-1.88 (m, 3H), 2.08-2.17 (m, 2H), 2.20-2.27 (m, 2H), 2.31-2.41 (m, 2H), 2.47 (t, 1H, J=2.0 Hz), 7.21-7.25 (m, 1H), 7.65 (d, 2H, J=8.8 Hz), 7.69-7.77 (m, 1H), 7.82 (d, 2H, J=9.2 Hz), 8.38 (d, 1H, J=4.0 Hz), 8.48 (s, 1H), 10.27 (s, 1H) and 12.57 (brs, 1H); $^{13}$C NMR (100 MHz, DMSO-d$_6$) δ 22.2, 23.7, 34.0, 52.7, 66.8, 118.2, 120.6, 123.6, 124.9, 129.9, 130.3, 134.8, 143.4, 148.4, 149.0, 167.0 and 171.5; Mass spectrum (FAB+), m/z 354.1819 (M+H)$^+$ (C$_{20}$H$_{24}$N$_3$O$_3$ requires m/z 354.1818).

(32)

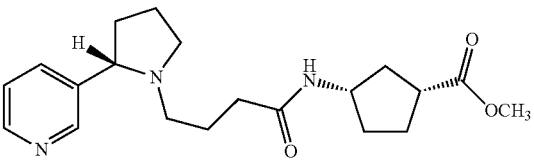

(1R,3S)-Methyl 3-(4-((S)-2-(pyridin-3-yl)pyrrolidin-1-yl)butanamido)cyclopentane-carboxylate (32)

To an ice-cool stirred solution of 7a (38 mg, 0.162 mmol) in dry DMF (0.6 mL) was added HBTU (68 mg, 0.179 mmol). After 10 min, a solution of 16 (35 mg, 0.195) and N-methylmorpholine (54 μL, 0.487 mmol) in dry DMF (0.3 mL) was added at 0° C. After 18 h at room temperature, the reaction mixture was diluted with water (20 mL), extracted with ethyl acetate (2×20 mL). The combined organic phase was washed with brine, dried over anhydrous MgSO$_4$ and concentrated under diminished pressure. The residue was purified by flash chromatography on a silica gel column (20×1 cm), eluting with 1:9 methanol-CH$_2$Cl$_2$ afforded 32 as a pale yellow oil: yield 27 mg (48%); silica gel TLC R$_f$ 0.25 (1:9 methanol-CH$_2$Cl$_2$); $^1$H NMR (400 MHz, CDCl$_3$) δ 1.42-1.49 (m, 1H), 1.54-1.61 (m, 1H), 1.66-1.88 (m, 7H), 1.93-2.21 (m, 5H), 2.22-2.55 (m, 3H), 2.71-2.78 (m, 1H), 3.34-3.47 (m, 2H), 3.57 (s, 3H), 4.12-4.18 (m, 1H), 6.40 (brs, 1H), 7.18 (t, 1H, J=2.8 Hz), 7.72 (s, 1H), 8.41 (d, 1H, J=4.0 Hz) and 8.45 (s, 1H); $^{13}$C NMR (100 MHz, CDCl$_3$) δ 22.4, 23.7, 28.3, 29.6, 32.9, 34.3, 36.0, 41.7, 50.8, 52.0, 53.3, 53.5, 68.1, 123.7, 135.4, 149.1, 149.5, 172.1 and 177.8; Mass spectrum (FAB+), m/z 360.2277 (M+H)$^+$ (C$_{20}$H$_{30}$N$_3$O$_3$ requires m/z 360.2287).

(33)

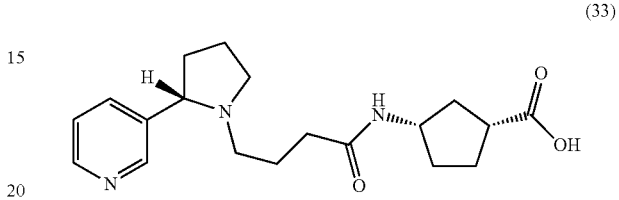

(1R,3S)-3-(4-((S)-2-(pyridin-3-yl)pyrrolidin-1-yl)butanamido)cyclopentanecarboxylic acid (33)

A solution of 32 (26 mg, 0.072 mmol) in methanol (0.5 mL) was added aq NaOH (9 mg, 0.217 mmol) with stirring at room temperature. After 18 h, the reaction mixture was evaporated, residue was dissolved in acetone (3 mL) and the pH was adjusted to 7 by using acetic acid. Acetone was evaporated under diminished pressure and the residue was directly purified by flash chromatography on a silica gel column (10×1 cm) eluting with 1:1.5 methanol-CH$_2$Cl$_2$ afforded 33 as a colorless oil: yield 19 mg (76%); silica gel TLC R$_f$ 0.2 (1:1.5 methanol-CH$_2$Cl$_2$); $^1$H NMR (400 MHz, CDCl$_3$) δ 1.42-1.51 (m, 1H), 1.61-1.91 (m, 9H), 2.00-2.27 (m, 6H), 2.37-2.44 (m, 1H), 2.70-2.84 (m, 1H), 3.30-3.39 (m, 2H), 4.22-4.27 (m, 1H), 6.96 (d, 1H, J=7.2 Hz), 7.27 (d, 1H, J=6.8 Hz), 7.68 (d, 1H, J=8.0 Hz), 8.41 (s, 1H), 8.65 (s, 1H) and 12.98 (brs, 1H); $^{13}$C NMR (100 MHz, CDCl$_3$) δ 22.8, 24.0, 28.3, 32.9, 34.3, 35.0, 36.3, 42.9, 50.8, 53.4, 53.7, 67.8, 123.9, 136.7, 139.9, 147.1, 148.3, 172.4 and 181.2; Mass spectrum (FAB+), m/z 346.2125 (M+H)$^+$ (C$_{19}$H$_{28}$N$_3$O$_3$ requires m/z 346.2131).

(34)

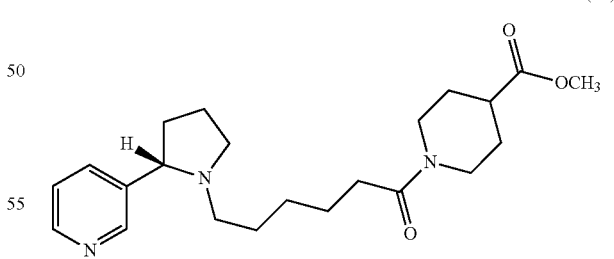

(S)-Methyl 1-(6-(2-(pyridin-3-yl)pyrrolidin-1-yl)hexanoyl)piperidine-4-carboxylate (34)

To an ice-cool stirred solution of 7b (65 mg, 0.248 mmol) in dry DMF (0.7 mL) was added HBTU (141 mg, 0.372 mmol). After 10 min, a solution of methyl piperidine-4-carboxylate (53 mg, 0.246 mmol) and N-methylmorpholine (82 μL, 0.744 mmol) in dry DMF (0.3 mL) was added at 0°

C. After 18 h at room temperature, the reaction mixture was diluted with water (20 mL), extracted with ethyl acetate (2×20 mL). The combined organic phase was washed with brine, dried over anhydrous MgSO$_4$ and concentrated under diminished pressure. The residue was further purified by flash chromatography on a silica gel column (15×2 cm) eluting with 5% methanol in CH$_2$Cl$_2$ afforded 34 as a pale yellow oil: yield 62 mg (65%); silica gel TLC R$_f$ 0.35 (5% methanol in CH$_2$Cl$_2$); $^1$H NMR (400 MHz, CDCl$_3$) δ 1.15-1.35 (m, 2H), 1.39-1.1.46 (m, 2H), 1.48-1.66 (m, 5H), 1.81-1.91 (m, 4H), 2.05-2.20 (m, 3H), 2.25 (t, 2H, J=8.0 Hz), 2.41-2.54 (m, 2H), 2.75 (t, 1H, J=12.0 Hz), 3.01-3.07 (m, 1H), 3.24 (s, 1H), 3.33 (s, 1H), 3.67 (s, 3H), 3.75 (d, 1H, J=13.6 Hz), 4.37 (d, 1H, J=13.2 Hz), 7.24 (s, 1H), 7.69 (s, 1H), 8.48 (s, 1H) and 8.53 (s, 1H); $^{13}$C NMR (100 MHz, CDCl$_3$) δ 22.7, 25.3, 27.3, 28.0, 28.6, 33.3, 35.1, 40.9, 41.0, 44.9, 51.9, 53.7, 54.3, 67.9, 123.8, 135.1, 148.6, 149.6, 171.4 and 174.8; Mass spectrum (APCI+), m/z 388.2607 (M+H)$^+$ (C$_{22}$H$_{34}$N$_3$O$_3$ requires m/z 388.2600).

(35)

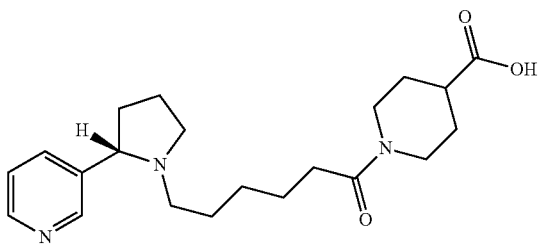

(S)-1-(6-(2-(Pyridin-3-yl)pyrrolidin-1-yl)hexanoyl)piperidine-4-carboxylic acid (35)

A solution of 34 (41 mg, 0.106 mmol) in methanol (0.6 mL) was added aq NaOH (13 mg, 0.318 mmol) with stirring at room temperature. After 18 h, the reaction mixture was evaporated, dissolved in 2 mL of acetone and the pH was adjusted to 7 by using acetic acid. Acetone was evaporated and the crude product was directly purified by flash chromatography on a silica gel column (10×1 cm), eluting with 1:1.5 methanol-CH$_2$Cl$_2$ afforded 35 as a pale yellow oil: yield 28 mg (75%); silica gel TLC R$_f$ 0.25 (1:1.5 methanol-CH$_2$Cl$_2$); $^1$H NMR (400 MHz, CDCl$_3$) δ 1.17-1.26 (m, 2H), 1.41-1.60 (m, 6H), 1.71-1.92 (m, 6H), 2.08-2.28 (m, 5H), 2.40-2.45 (m, 2H), 2.74 (t, 2H), 3.02 (t, 2H), 3.30-3.35 (m, 2H), 3.70 (d, 1H), 4.36 (d, 1H), 7.28 (s, 1H), 7.76 (d, 1H), 8.51 (d, 2H) and 10.12 (brs, 1H). $^{13}$C NMR (100 MHz, CDCl$_3$) δ 22.4, 25.1, 27.1, 27.9, 28.2, 28.8, 33.1, 34.5, 41.2, 45.1, 45.1, 53.3, 54.0, 67.7, 136.1, 147.6, 148.5 and 171.5; Mass spectrum (APCI+), m/z 374.2438 (M+H)$^+$ (C$_{21}$H$_{32}$N$_3$O$_3$ requires m/z 374.2444).

(36)

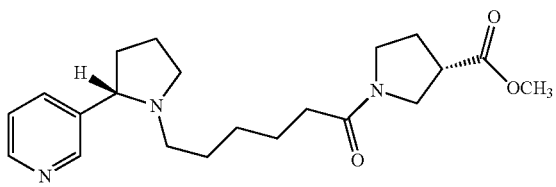

(S)-Methyl 1-(6-((S)-2-(pyridin-3-yl)pyrrolidin-1-yl)hexanoyl)pyrrolidine-3-carboxylate (36)

To an ice-cool stirred solution of 7b (50 mg, 0.191 mmol) in dry DMF (0.7 mL) was added HBTU (108 mg, 0.286 mmol). After 10 min, a solution of (S)-methyl pyrrolidine-3-carboxylate (37 mg, 0.286 mmol) and N-methylmorpholine (63 µL, 0.573 mmol) in dry DMF (0.3 mL) was added at 0° C. After 18 h at room temperature, the reaction mixture was diluted with water (20 mL), extracted with ethyl acetate (2×20 mL). The combined organic phase was washed with brine, dried over anhydrous MgSO$_4$ and concentrated under diminished pressure. The residue was further purified by flash chromatography on a silica gel column (15×1 cm) eluting with 5% methanol in CH$_2$Cl$_2$ afforded 36 as a pale yellow oil: yield 30 mg (42%); silica gel TLC R$_f$ 0.35 (5% methanol in CH$_2$Cl$_2$); $^1$H NMR (400 MHz, CDCl$_3$) δ 1.17-1.27 (m, 2H), 1.46-1.58 (m, 6H), 1.86-1.89 (m, 2H), 2.00-2.25 (m, 8H), 2.38-2.50 (m, 1H), 2.51-2.54 (m, 1H), 2.97-3.00 (m, 1H), 3.06-3.16 (m, 1H), 3.35-3.40 (m, 1H), 3.45-3.58 (m, 4H), 3.60-3.68 (m, 4H (3+1)), 7.24 (d, 1H, J=6.0 Hz), 7.88 (s, 1H), 8.46 (d, 1H, J=4.8 Hz) and 8.52 (s, 1H); $^{13}$C NMR (100 MHz, CDCl$_3$) δ 22.2, 24.3, 27.0, 27.7, 29.1, 34.2, 41.6, 42.5, 45.0, 48.5, 52.3, 53.5, 53.9, 68.3, 123.8, 135.7, 149.2, 149.8, 171.4 and 173.5; Mass spectrum (FAB+), m/z 374.2442 (M+H)$^+$ (C$_{21}$H$_{32}$N$_3$O$_3$ requires m/z 374.2444).

(37)

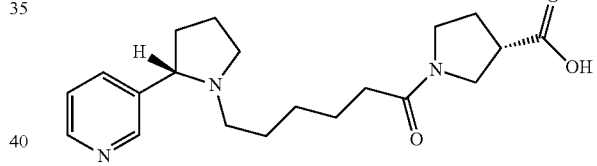

(S)-1-(6-((S)-2-(Pyridin-3-yl)pyrrolidin-1-yl)hexanoyl)pyrrolidine-3-carboxylic acid (37)

A solution of 36 (30 mg, 0.08 mmol) in methanol (0.6 mL) was added aq NaOH (9.7 mg, 0.24 mmol) with stirring at room temperature. After 18 h, the reaction mixture was evaporated, dissolved in 2 mL of acetone and the pH was adjusted to 7 by using acetic acid. Acetone was evaporated and the crude product was directly purified by flash chromatography on a silica gel column (10×1 cm), eluting with 1:1.5 methanol-CH$_2$Cl$_2$ afforded 37 as a pale yellow oil: yield 18 mg (62%); silica gel TLC R$_f$ 0.25 (1:1.5 methanol-CH$_2$Cl$_2$); $^1$H NMR (400 MHz, CDCl$_3$) δ 1.07-1.24 (m, 1H), 1.28-1.91 (m, 7H), 1.92-2.40 (m, 8H), 2.93-3.11 (m, 1H), 3.31-3.48 (m, 3H), 3.49-3.68 (m, 2H), 7.30 (dd, 1H, J=7.4, 8.2 Hz), 7.71 (d, 1H, J=7.8 Hz), 8.45 (d, 1H, J=4.6 Hz) and 8.57 (s, 1H); $^{13}$C NMR (100 MHz, CDCl$_3$) δ 22.4, 24.9, 27.0, 27.8, 28.3, 33.8, 45.0, 46.0, 48.9, 49.5, 52.9, 53.1, 67.8, 123.9, 136.6, 147.6, 148.8 and 171.7; Mass spectrum (APCI+), m/z 360.2294 (M+H)$^+$ (C$_{20}$H$_{30}$N$_3$O$_3$ requires m/z 360.2287).

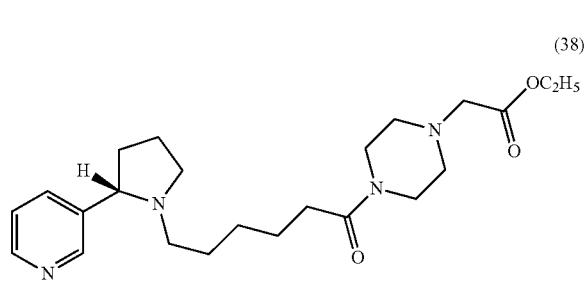 [SMILES: CCOC(=O)CN1CCN(C(=O)CCCCCN2CCC[C@H]2c2cccnc2)CC1]

(38)

(S)-Ethyl 2-(4-(6-(2-(pyridin-3-yl)pyrrolidin-1-yl)hexanoyl)piperazin-1-yl)acetate (38)

To an ice-cool stirred solution of 7b (50 mg, 0.191 mmol) in dry DMF (0.7 mL) was added HBTU (108 mg, 0.286 mmol). After 10 min, a solution of 19 (49 mg, 0.286 mmol) and N-methylmorpholine (63 µL, 0.573 mmol) in dry DMF (0.3 mL) was added at 0° C. After 18 h at room temperature, the reaction mixture was diluted with water (20 mL), extracted with ethyl acetate (2×20 mL). The combined organic phase was washed with brine, dried over anhydrous MgSO$_4$ and concentrated under diminished pressure. The residue was further purified by flash chromatography on a silica gel column (15×2 cm) eluting with 10% methanol in CH$_2$Cl$_2$ afforded 38 as a pale yellow oil: yield 42 mg, (53%); silica gel TLC R$_f$ 0.17 (10% methanol in CH$_2$Cl$_2$); $^1$H NMR (400 MHz, CDCl$_3$) δ 1.16-1.40 (m, 5H), 1.45-1.64 (m, 4H), 1.92 (brs, 2H), 2.06 (brs, 1H), 2.24-2.28 (m, 4H), 2.39 (brs, 1H), 2.53-2.65 (m, 4H), 3.23 (s, 2H), 3.48 (m, 3H), 3.65 (t, 2H, J=5.2 Hz), 4.19 (q, 2H, J=7.2, 14.4 Hz), 7.25-7.33 (dd, 1H, J=5.2, 6.0 Hz), 7.76-7.97 (m, 1H), 8.52 (d, 1H, J=4.0 Hz) and 8.57 (d, 1H, J=1.6 Hz); $^{13}$C NMR (100 MHz, CDCl$_3$) δ 14.3, 22.4, 25.0, 27.1, 33.0, 41.4, 45.4, 52.6, 53.0, 53.6, 54.1, 59.2, 60.8, 123.7, 135.5, 149.8, 170.0 and 171.4; Mass spectrum (APCI+), m/z 417.2868 (M+H)$^+$ (C$_{23}$H$_{37}$N$_4$O$_3$ requires m/z 417.2866).

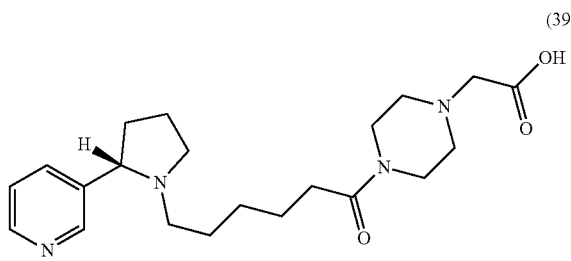

(39)

(S)-2-(4-(6-(2-(Pyridin-3-yl)pyrrolidin-1-yl)hexanoyl)piperazin-1-yl)acetic acid (39)

A solution of 38 (40 mg, 0.10 mmol) in methanol (0.6 mL) was added aq NaOH (12 mg, 0.29 mmol) with stirring at room temperature. After 18 h, the reaction mixture was evaporated, dissolved in 1 mL of acetone and the pH was adjusted to 7 by using acetic acid. Acetone was evaporated and the crude product was directly purified by flash chromatography on a silica gel column (10×1 cm), eluting with 1:1.5 methanol-CH$_2$Cl$_2$ afforded 39 as a pale yellow oil: yield 19 mg (49%); silica gel TLC R$_f$ 0.2 (1:1.5 methanol-CH$_2$Cl$_2$); $^1$H NMR (400 MHz, CDCl$_3$) δ 1.16-1.36 (m, 2H), 1.39-1.54 (m, 4H), 1.63-1.71 (m, 1H), 1.79-1.87 (m, 1H), 1.90-1.96 (m, 1H), 2.04-2.11 (m, 1H), 2.13-2.26 (m, 4H), 2.41-2.48 (m, 5H), 3.00 (brs, 2H), 3.27 (t, 1H, J=8.4 Hz), 3.33 (t, 1H, J=7.6 Hz), 3.47 (brs, 2H), 3.61 (brs, 2H), 7.23-7.26 (dd, 1H, J=4.8, 7.2 Hz), 7.69 (d, 1H, J=8.0 Hz), 8.46 (d, 1H, J=3.6 Hz) and 8.54 (s, 1H); $^{13}$C NMR (100 MHz, CDCl$_3$) δ 22.6, 25.1, 27.2, 28.5, 32.0, 35.0, 40.8, 44.8, 53.0, 53.5, 54.2, 67.7, 123.6, 135.3, 139.6, 148.2, 149.2 and 171.4; Mass spectrum (APCI+), m/z 389.2563 (M+H)$^+$ (C$_{21}$H$_{33}$N$_4$O$_3$ requires m/z 389.2553).

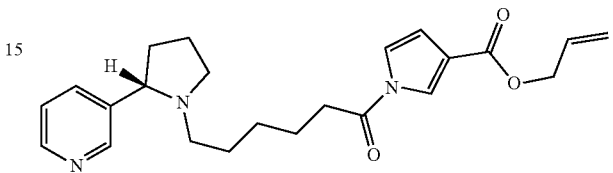

(40)

(S)-Allyl 1-(6-(2-(pyridin-3-yl)pyrrolidin-1-yl)hexanoyl)-1H-pyrrole-3-carboxylate (40)

To a stirred solution of (S)-6-(2-(pyridin-3-yl)pyrrolidin-1-yl)hexanoic acid (7b, 72 mg, 0.275 mmol) and a drop of DMF in dry CH$_2$Cl$_2$ (2 mL) was added oxalyl chloride (47 µL, 0.550 mmol). After 2 h at room temperature, reaction mixture was concentrated under reduced pressure yielded the acid chloride. This acid chloride was dissolved in DCM (2 mL) and added drop wise to a stirred solution containing allyl 1H-pyrrole-3-carboxylate (21, 46 mg, 0.30 mmol), DMAP (19 mg, 0.152 mmol) and diisopropylethylamine (159 µL, 0.913 mmol) in dry CH$_2$Cl$_2$ (5 mL). The reaction mixture was stirred for 18 h at room temperature. The reaction mixture was diluted with CH$_2$Cl$_2$ (20 mL), washed with aq satd NaHCO$_3$ (10 mL), water, brine, dried over anhydrous MgSO$_4$ and concentrated under diminished pressure. The residue was purified by a flash chromatography on a silica gel column (20×2 cm) eluting with 1:19 methanol-CH$_2$Cl$_2$ afforded 40 as a pale yellow oil: yield 54 mg (50%); silica gel TLC R$_f$ 0.31 (1:19 methanol-CH$_2$Cl$_2$); $^1$H NMR (400 MHz, CDCl$_3$) δ 1.27-1.50 (m, 4H), 1.62-1.74 (m, 3H), 1.80-1.87 (m, 1H), 1.89-1.97 (m, 1H), 2.06-2.25 (m, 3H), 2.44-2.51 (m, 1H), 2.79 (t, 2H, J=7.6 Hz), 3.25 (t, 1H, J=8.0 Hz), 3.33 (t, 1H, J=6.4 Hz), 4.75 (t, 2H, J=6.0 Hz), 5.27 (d, 1H, J=12.0 Hz), 5.37 (d, 1H, J=17.2 Hz), 5.96-6.05 (m, 1H), 6.68 (s, 1H), 7.23-7.29 (m, 2H), 7.69 (d, 1H, J=7.6 Hz), 7.88 (s, 1H), 8.49 (s, 1H) and 8.55 (s, 1H); $^{13}$C NMR (100 MHz, CDCl$_3$) δ 22.7, 24.2, 26.8, 28.5, 34.4, 35.2, 53.7, 54.1, 65.0, 67.7, 112.9, 118.2, 119.7, 120.2, 123.7, 132.4, 134.9, 148.5, 149.5, 163.6 and 170.4; Mass spectrum (APCI+), m/z 396.2280 (M+H)$^+$ (C$_{23}$H$_{30}$N$_3$O$_3$ requires m/z 396.2287).

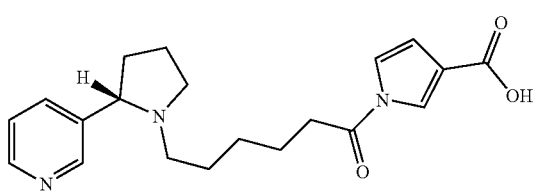

(41)

(S)-1-(6-(2-(Pyridin-3-yl)pyrrolidin-1-yl)hexanoyl)-1H-pyrrole-3-carboxylic acid (41)

To a stirred solution of 40 (52 mg, 0.132 mmol) in dry CH$_2$Cl$_2$ (5 mL) was added phenyl silane (243 μL, 1.97 mmol) and Pd(PPh$_3$)$_4$ (15 mg, 0.013 mmol) at room temperature. After 1 h, the reaction mixture was concentrated under diminished pressure and the residue was directly purified by flash chromatography on a silica gel column (15×1 cm) eluting 1:1.5 methanol-CH$_2$Cl$_2$ afforded 41 as a pale yellow oil: yield 31 mg (66%); silica gel TLC R$_f$ 0.28 (1:1.5 methanol-CH$_2$Cl$_2$); $^1$H NMR (400 MHz, CDCl$_3$) δ 1.25-1.45 (m, 4H), 1.51-1.65 (m, 2H), 1.66-1.77 (m, 1H), 1.78-1.88 (m, 1H), 1.89-2.03 (m, 1H), 2.05-2.24 (m, 2H), 2.26-2.34 (m, 1H), 2.37-2.51 (m, 1H), 2.58-2.80 (m, 2H), 3.25-3.43 (m, 2H), 6.59 (s, 1H), 7.18 (s, 1H), 7.29 (s, 1H), 7.78 (s, 1H), 7.79 (s, 1H), 8.51 (s, 1H), 8.61 (s, 1H) and 11.89 (brs, 1H); $^{13}$C NMR (100 MHz, CDCl$_3$) δ 22.6, 24.0, 26.6, 27.9, 34.1, 34.7, 53.4, 53.9, 67.8, 113.3, 119.1, 123.5, 123.8, 135.9, 139.1, 147.9, 148.8 and 170.5; Mass spectrum (APCI+), m/z 356.1967 (M+H)$^+$ (C$_{20}$H$_{26}$N$_3$O$_3$ requires m/z 356.1974).

tert-Butyl 4-((5-hydroxypentyl)carbamoyl)piperidine-1-carboxylate (44)

To an ice-cool stirred solution of 42 (580 mg, 2.53 mmol) in dry THF (15 mL) was added trimethylamine (1.05 mL, 7.59 mmol) and N,N'-disuccinimidyl carbonate (971 mg, 3.79 mmol). The reaction mixture was stirred at room temperature for 3 hours and filtered. To the filtrate was added 5-aminopentan-1-ol (390 mg, 3.79 mmol) and stirred for 3 h. The reaction mixture was diluted with CH$_2$Cl$_2$ (100 mL), washed with water, brine, dried over MgSO$_4$ and concentrated under diminished pressure. The crude product was purified by chromatography on silica gel column (20×4 cm) by eluting with DCM/methanol (19:1) to give 44 as a colorless oil: yield 384 mg (80%); silica gel TLC R$_f$ 0.27 (5% MeOH in CH$_2$Cl$_2$); $^1$H NMR (400 MHz, CDCl$_3$) δ 1.34-1.42 (m, 2H), 1.45 (s, 9H), 1.48-1.66 (m, 6H), 1.77 (d, 2H, J=11.2 Hz), 2.25-232 (m, 1H), 2.71-2.75 (m, 3H), 3.22 (q, 2H, J=6.8, 13.2 Hz), 3.60 (t, 2H, J=6.4 Hz), 4.11 (d, 2H, J=12.0 Hz) and 6.55 (t, 1H, J=5.6 Hz); $^{13}$C NMR (100 MHz, CDCl$_3$) δ 23.0, 25.4, 28.4, 28.6, 29.1, 32.0, 39.3, 43.1, 62.2, 79.8, 154.8 and 175.1.

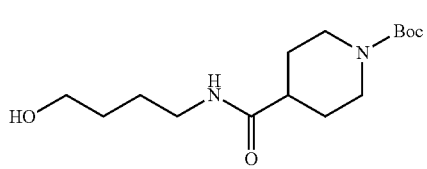

(43)

tert-Butyl 4-((4-hydroxybutyl)carbamoyl)piperidine-1-carboxylate (43)

To an ice-cool stirred solution of 42 (650 mg, 2.84 mmol) in dry THF (15 mL) was added trimethylamine (1.18 mL, 8.49 mmol) and N,N'-disuccinimidyl carbonate (1.14 g, 4.25 mmol). The reaction mixture was stirred at room temperature for 3 h and filtered. To the filtrate was added 4-aminobutan-1-ol (378 mg, 4.25 mmol) and stirred for 3 h. The reaction mixture was diluted with CH$_2$Cl$_2$ (100 mL), washed with water, brine, dried over MgSO$_4$ and concentrated under diminished pressure. The residue was purified by chromatography on a silica gel column (20×4 cm) eluting with 1:19 methanol-CH$_2$Cl$_2$ afforded 43 as a colorless oil: yield 690 mg (81%); silica gel TLC R$_f$ 0.27 (1:19 methanol-CH$_2$Cl$_2$); $^1$H NMR (400 MHz, CDCl$_3$) δ 1.45 (s, 9H), 1.54-1.76 (m, 6H), 1.77-1.81 (m, 1H), 2.19-2.27 (m, 1H), 2.73 (t, 2H, J=11.6 Hz), 2.90 (brs, 1H), 3.28 (q, 2H, J=6.4, 12.4 Hz), 3.66 (t, 2H, J=6.0 Hz), 4.12 (d, 2H, J=9.2 Hz) and 6.25 (t, 1H, J=5.6 Hz); $^{13}$C NMR (100 MHz, CDCl$_3$) δ 26.3, 28.4, 28.7, 29.7, 39.2, 43.3, 62.1, 79.7, 154.7 and 174.7; Mass spectrum (FAB+), m/z 301.2134 (M+H)$^+$ (C$_{15}$H$_{29}$N$_2$O$_4$ requires m/z 301.2127).

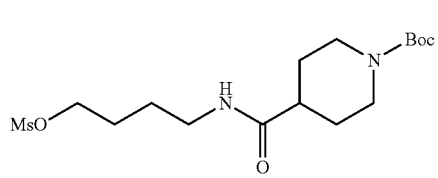

(45)

tert-Butyl 4-((4-((methylsulfonyl)oxy)butyl)carbamoyl)piperidine-1-carboxylate (45)

To an ice-cool stirred solution of 43 (400 mg, 1.33 mmol) in dry CH$_2$Cl$_2$ (5 mL) was added triethylamine (0.56 mL, 3.99 mmol) and methanesulfonyl chloride (0.16 mL, 2.00 mmol). After 2 hours at room temperature, reaction mixture was diluted with CH$_2$Cl$_2$ (40 mL), washed with satd aq NaHCO$_3$, water, brine, dried over anhydrous MgSO$_4$ and concentrated under diminished pressure. The residue was purified by chromatography on a silica gel column (15×2 cm) eluting with 4:1 ethyl acetate-hexanes afforded 45 as a colorless oil: yield 430 mg (85%); silica gel TLC R$_f$ 0.56 (19:1 dichloromethane-methanol); $^1$H NMR (400 MHz, CDCl$_3$) δ 1.45 (s, 9H), 1.60-1.67 (m, 4H), 1.74-1.80 (m, 4H), 2.22-2.28 (m, 1H), 2.73 (brs, 2H), 3.03 (s, 3H), 3.28 (q, 2H, J=6.8, 12.8 Hz), 4.13 (brs, 2H), 4.25 (t, 2H, J=6.4 Hz) and 6.18 (t, 1H, J=5.2 Hz); $^{13}$C NMR (100 MHz, CDCl$_3$) δ 25.7, 26.5, 28.4, 28.6, 37.3, 38.5, 43.2, 69.8, 79.6, 154.7 and 174.7; Mass spectrum (APCI+), m/z 379.1910 (M+H)$^+$ (C$_{16}$H$_{31}$N$_2$O$_6$S requires m/z 379.1903).

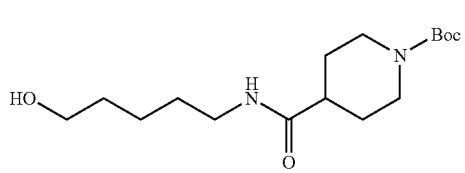

(44)

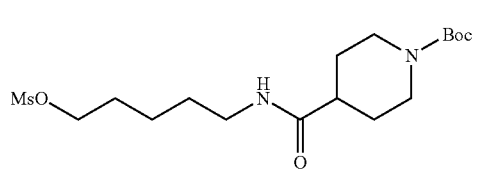

(46)

tert-Butyl 4-((5-((methylsulfonyl)oxy)pentyl)carbamoyl)piperidine-1-carboxylate (46)

To a solution of compound 44 (380 mg, 1.21 mmol) in dichloromethane (5 mL) was added triethylamine (422 µL, 3.02 mmol) and methanesulfonyl chloride (122 µL, 1.57 mmol) at 0° C. The reaction mixture was warmed to room temperature, stirred for 2 hours, and extracted with dichloromethane and water. The organic layer was washed with sat. NaHCO$_3$ solution, brine, dried over anhydrous magnesium sulfate and concentrated. The crude was purified through chromatography with silica gel eluting with 1:4 hexanes-ethyl acetate to give compound 46 as a pale yellow oil; yield 426 mg (90%); silica gel TLC R$_f$ 0.56 (19:1 dichloromethane-methanol); $^1$H NMR (400 MHz, CDCl$_3$) δ 1.42-1.48 (m, 9+2 H, 1.52-1.58 (m, 2H), 1.60-1.67 (m, 2H), 1.75-1.81 (m, 4H), 2.22-2.28 (m, 1H), 2.72 (d, 2H, J=10.4 Hz), 3.02 (s, 3H), 3.24 (q, 2H, J=6.8, 12.8 Hz), 4.12 (d, 2H, J=10.0 Hz), 4.23 (t, 2H, J=6.0 Hz) and 6.15 (t, 1H, J=6.0 Hz); $^{13}$C NMR (100 MHz, CDCl$_3$) δ 22.7, 28.4, 28.6, 28.7, 28.9, 37.3, 38.9, 43.1, 70.0, 79.5, 154.7 and 174.6.

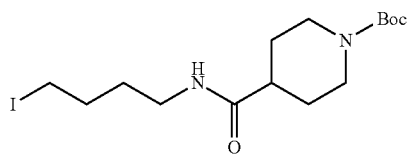

(47)

tert-Butyl 4-((4-iodobutyl)carbamoyl)piperidine-1-carboxylate (47)

A mixture of 45 (430 mg, 1.14 mmol) and sodium iodide (750 mg, 5.68 mmol) in acetonitrile (2 mL) was vigorously stirred at room temperature. After 18 hours, the mixture was evaporated and the residue was partitioned between ethyl acetate and water. The organic phase was washed with aq Na$_2$S$_2$O$_3$ solution, water, brine, dried over MgSO$_4$ and concentrated under diminished pressure. The residue was purified by chromatography on a silica gel column (15×2 cm) eluting with 1:1 ethyl acetate-hexanes afforded 47 as a pale yellow oil (290 mg, 62% yield); silica gel TLC R$_f$ 0.66 (4:1 ethyl acetate-hexanes); $^1$HNMR (400 MHz, CDCl$_3$) δ 1.45 (s, 9H), 1.58-1.67 (m, 4H), 1.77-1.86 (m, 4H), 2.20-2.27 (m, 1H), 3.20 (t, 2H, J=6.8 Hz), 3.25-3.30 (q, 2H, J=6.8, 13.2 Hz), 4.13 (d, 2H, J=6.4 Hz) and 5.94 (s, 1H); $^{13}$C NMR (100 MHz, CDCl$_3$) δ 6.2, 28.4, 28.7, 30.5, 30.6, 38.2, 43.3, 79.6, 154.6 and 174.5; Mass spectrum (APCI+), m/z 411.1148 (M+H)$^+$ (C$_{15}$H$_{28}$N$_2$O$_3$I requires m/z 411.1145).

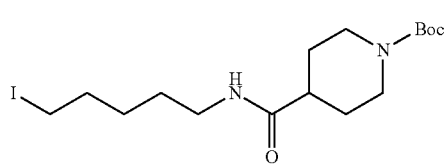

(48)

tert-Butyl 4-((5-iodopentyl)carbamoyl)piperidine-1-carboxylate (48)

A mixture of 46 (420 mg, 1.07 mmol) and sodium iodide (802 mg, 5.35 mmol) in acetonitrile (6 mL) was vigorously stirred at room temperature. After 18 hours, the mixture was evaporated and the residue was partitioned between ethyl acetate and water. The EtOAc layer was washed with Na$_2$S$_2$O$_3$ solution, water, brine, dried over MgSO$_4$, and evaporated. The residue was purified by chromatography on silica gel eluting with 3:2 hexanes-ethyl acetate to give 48 as a pale yellow oil: yield 293 mg (65%); silica gel TLC R$_f$ 0.66 (1:4 hexanes-ethyl acetate); $^1$H NMR (400 MHz, CDCl$_3$) δ 1.38-1.45 (m, 9+2 H, 1.49-1.55 (m, 2H), 1.61-1.69 (m, 2H), 1.77-1.86 (m, 4H), 2.24-2.28 (m, 1H), 2.26 (d, 2H), 3.19 (t, 2H, J=7.2 Hz), 3.24 (q, 2H, J=6.8, 12.8 Hz), 4.12 (d, 2H, J=8.0 Hz) and 6.16 (t, 1H); $^{13}$C NMR (100 MHz, CDCl$_3$) δ 6.9, 27.6, 28.4, 28.5, 28.6, 32.8, 39.0, 43.2, 79.6, 154.6 and 174.5.

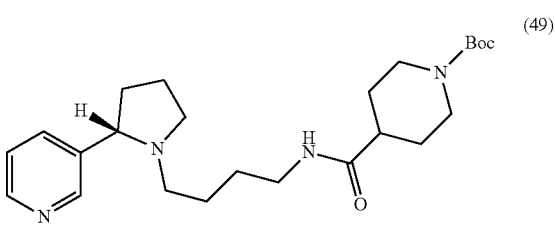 [SMILES: CC(C)(C)OC(=O)N1CCC(C(=O)NCCCCN2CCC[C@H]2c2cccnc2)CC1]

(49)

(S)-tert-Butyl 4-((4-(2-(pyridin-3-yl)pyrrolidin-1-yl)butyl)carbamoyl)piperidine-1-carboxylate (49)

A solution of 47 (198 mg, 0.48 mmol) in acetonitrile (0.3 mL) was added to a stirred solution of 5 (65 mg, 0.44 mmol) and diisopropylethylamine (153 µL, 0.88 mmol) in acetonitrile (0.8 mL) at room temperature. After 18 hours, reaction mixture was concentrated under diminished pressure, residue was directly purified by flash chromatography on a silica gel column (15×2 cm) eluting with 10% methanol in CH$_2$Cl$_2$ afforded 49 as a pale yellow oil: yield 95 mg (51%); silica gel TLC R$_f$ 0.16 (9:1 dichloromethane-methanol); $^1$H NMR (400 MHz, CDCl$_3$) δ 1.38-1.65 (m, 9H+6H), 1.75-1.78 (m, 3H), 1.87-1.91 (m, 1H), 1.93-2.01 (m, 1H), 2.15-2.33 (m, 4H), 2.50-2.53 (m, 1H), 2.73 (t, 2H, J=12.0 Hz), 3.13-3.17 (m, 2H), 3.42 (brs, 2H), 4.12 (brs 2H), 5.76 (s, 1H), 7.26 (d, 1H, J=6.0 Hz), 7.79 (s, 1H), 8.51 (d, 1H, J=3.6 Hz) and 8.56 (d, 1H, J=1.6 Hz); $^{13}$C NMR (100 MHz, CDCl$_3$) δ 22.5, 25.6, 27.4, 28.4, 28.7, 28.7, 34.7, 39.0, 43.4, 53.5, 53.84, 79.6, 123.6, 135.3, 148.9, 149.6, 154.7 and 174.4; Mass spectrum (APCI+), m/z 431.3024 (M+H)$^+$ (C$_{24}$H$_{39}$N$_4$O$_3$ requires m/z 431.3022).

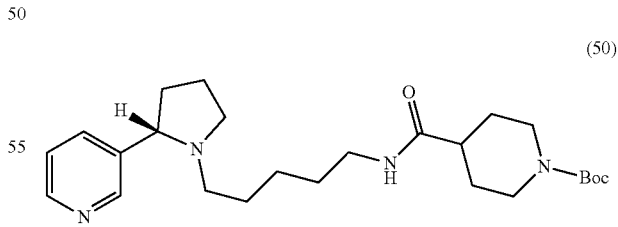

(50)

(S)-tert-Butyl 4-((5-(2-(pyridin-3-yl)pyrrolidin-1-yl)pentyl)carbamoyl)piperidine-1-carboxylate (50)

A solution of 48 (241 mg, 0.567 mmol) in acetonitrile (0.5 mL) was added to a mixture of 5 (70 mg, 0.472 mmol) and diisopropylethylamine (206 µL, 1.18 mmol) in acetonitrile (1 mL) with stirring at room temperature. After 18 hours, the mixture was evaporated and the residue was purified by chromatography on silica gel eluting with 9:1 dichloromethane-methanol to give product 50 as a pale yellow oil: yield 102 mg (49%); silica gel TLC R$_f$ 0.16 (9:1 dichloromethane-methanol); $^1$H NMR (500 MHz, CDCl$_3$) δ 1.15-1.23 (m, 1H), 1.24-1.35 (m, 1H), 1.39-1.49 (m, 13H (9+4)), 1.77 (t, 3H, J=9.6 Hz), 1.84-1.96 (m, 1H), 1.97-2.08 (m, 1H), 2.19-2.34 (m, 3H), 2.36-2.46 (m, 1H), 2.48-2.58 (m, 1H), 2.65-2.81 (m, 2H), 3.18 (d, 2H, J=5.8 Hz), 3.24 (d, 1H, J=7.3 Hz), 3.45-3.61 (m, 3H), 3.79-3.83 (m, 1H), 4.11 (brs, 2H), 6.19 (s, 1H), 7.29 (s, 1H), 7.83 (s, 1H), 8.50 (s, 1H), 8.59 (s, 1H); $^{13}$C NMR (125 MHz, CDCl$_3$) δ 12.4, 22.5, 24.5, 27.7, 28.4, 28.6, 29.2, 34.6, 39.1, 43.1, 53.5, 54.8, 68.0, 79.4, 123.7, 135.4, 148.8, 149.6, 154.6 and 174.5.

(51)

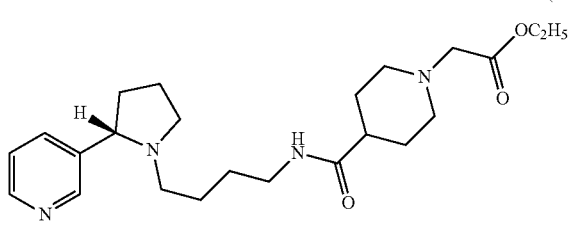

(S)-Ethyl 2-(4-((4-(2-(pyridin-3-yl)pyrrolidin-1-yl)butyl)carbamoyl)piperidin-1-yl)acetate (51)

To an ice-cooled stirred solution of 49 (95 mg, 0.22 mmol) in dry CH$_2$Cl$_2$ (2 mL) was added trifluoroacetic acid (0.25 mL, 3.31 mmol). After 18 hours at room temperature, reaction mixture was co-evaporated with 1 mL of toluene (3 times) yielded (S)—N-(4-(2-(pyridin-3-yl)pyrrolidin-1-yl)butyl)piperidine-4-carboxamide, which was directly used for the next reaction without any further purification. A solution of ethyl iodoacetate (71 mg, 0.33 mmol) in acetonitrile (0.2 mL) was added to a stirred solution of (S)—N-(4-(2-(pyridin-3-yl)pyrrolidin-1-yl)butyl)piperidine-4-carboxamide in acetonitrile (2 mL) and DIPEA (157 µL, 0.90 mmol) at room temperature. After 18 h, the reaction mixture was evaporated under diminished pressure. The residue was purified by flash chromatography on a silica gel column (15×1 cm) eluting with 1:9 methanol-CH$_2$Cl$_2$ afforded 51 as a pale yellow oil: yield 21 mg (28%); silica gel TLC R$_f$ 0.12 (9:1 dichloromethane-methanol); $^1$H NMR (400 MHz, CDCl$_3$) δ 1.27 (t, 3H, J=7.2 Hz), 1.36-1.51 (m, 4H), 1.70-1.88 (m, 6H), 1.93-1.99 (m, 1H), 2.02-2.09 (m, 1H), 2.13-2.26 (m, 5H), 2.43-2.48 (m, 1H), 2.97 (d, 2H, J=11.2 Hz), 3.13-3.19 (q, 2H, J=7.2, 14.4 Hz), 3.27-3.37 (m, 2H), 4.15-4.21 (q, 2H, J=7.6, 14.4 Hz), 5.66 (s, 1H), 7.25 (d, 1H, J=7.2 Hz), 7.72 (d, 1H, J=6.8 Hz), 8.50 (s, 1H) and 8.55 (s, 1H); $^{13}$C NMR (100 MHz, CDCl$_3$) δ 14.2, 22.6, 25.9, 27.5, 28.9, 35.0, 39.1, 42.9, 52.8, 53.5, 53.9, 59.7, 60.5, 67.9, 123.7, 135.0, 148.6, 149.5, 170.4 and 174.7; Mass spectrum (FAB+), m/z 417.2880 (M+H)$^+$ (C$_{23}$H$_{37}$N$_4$O$_3$ requires m/z 417.2866).

(S)-Ethyl 2-(4-((5-(2-(pyridin-3-yl)pyrrolidin-1-yl)pentyl)carbamoyl)piperidin-1-yl)acetate (52)

To a stirred solution of 50 (100 mg, 0.225 mmol) in dry DCM was added TFA (258 µL, 3.37 mmol). After 3 h the reaction mixture was co-evaporated with toluene (3 times) to give boc deprotected compound, which was directly used for the next reaction. A solution of ethyl iodoacetate (128 mg, 0.331 mmol) in acetonitrile (0.2 mL) was added to a stirred solution of boc deprotected compound and DIPEA (157 µL, 0.90 mmol) in acetonitrile (2 mL). After 18 hours, the reaction mixture was evaporated under diminished pressure. The residue was directly purified by chromatography on silica gel column (15×1 cm) eluting with 9:1 dichloromethane-methanol to give compound 52 as a pale yellow oil: yield 36 mg (37%); silica gel TLC R$_f$ 0.12 (9:1 dichloromethane-methanol); $^1$H NMR (500 MHz, CDCl$_3$) δ 1.11-1.25 (m, 6H), 1.29-1.35 (m, 2H), 1.41 (brs, 2H), 1.69-1.83 (m, 5H), 1.99-2.04 (m, 2H), 2.16-2.19 (m, 3H), 2.27-2.29 (m, 1H), 2.46 (brs, 1H), 2.90 (d, 2H, J=11.2 Hz), 3.09-3.12 (m, 2H), 3.14 (s, 2H), 3.37 (brs, 2H), 4.08-4.13 (m, 3H), 5.59 (s, 1H), 7.23 (s, 1H), 7.77 (s, 1H), 8.45 (s, 1H) and 8.49 (s, 1H); $^{13}$C NMR (125 MHz, CDCl$_3$) δ 13.2, 21.4, 27.8, 28.2, 28.7, 38.1, 41.8, 51.8, 52.5, 52.8, 58.6, 59.5, 122.7, 134.3, 148.7, 169.4 and 173.7;

(53)

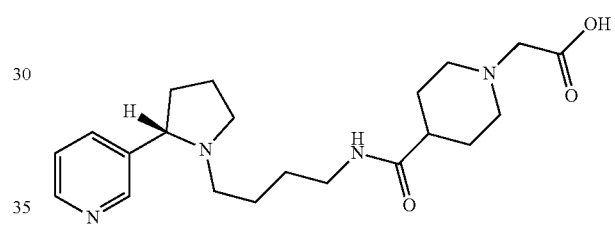

(S)-2-(4-((4-(2-(Pyridin-3-yl)pyrrolidin-1-yl)butyl)carbamoyl)piperidin-1-yl)acetic acid (53)

A solution of 51 (20 mg, 0.048 mmol) in methanol (0.5 mL) was added aq NaOH (6 mg, 0.144 mmol) with stirring at room temperature. After 18 hours, the reaction mixture was evaporated, dissolved in 1 mL of acetone and the pH was adjusted to 7 by using acetic acid. Acetone was evaporated and the crude product was directly purified by flash chromatography on a silica gel column (10×1 cm), eluting with 1:1 methanol-CH$_2$Cl$_2$ afforded 53 as a pale yellow oil: yield 13 mg (66%); silica gel TLC R$_f$ 0.12 (1:1 methanol-CH$_2$Cl$_2$); $^1$H NMR (400 MHz, CDCl$_3$) δ 1.20-1.51 (m, 4H), 1.52-1.61 (m, 1H), 1.62-2.00 (m, 7H), 2.12-2.36 (m, 6H), 3.03-3.23 (m, 8H), 7.18 (s, 1H), 7.47 (brs, 1H), 7.61 (d, 1H, J=7.2 Hz), 8.38 (d, 1H, J=2.0 Hz) and 8.46 (s, 1H); $^{13}$C NMR (100 MHz, CDCl$_3$) δ 22.8, 26.4, 27.1, 27.6, 35.3, 39.4, 52.7, 53.6, 54.1, 67.7, 123.7, 135.2, 139.9, 148.4, 149.3 and 174.6; Mass spectrum (FAB+), m/z 389.2552 (M+H)$^+$ (C$_{21}$H$_{33}$N$_4$O$_3$ requires m/z 389.2553).

(52)

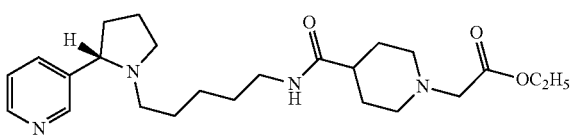

(54)

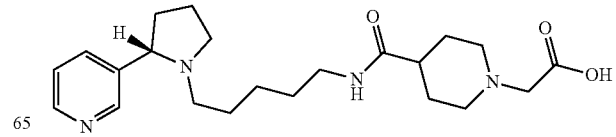

(S)-2-(4-((5-(2-(Pyridin-3-yl)pyrrolidin-1-yl)pentyl)carbamoyl)piperidin-1-yl)acetic acid (54)

A solution of 52 (34 mg, 0.079 mmol) in methanol (1 mL) was added aq NaOH (9.5 mg, 0.237 mmol) with stirring at room temperature. After 18 hours, the reaction mixture was evaporated, dissolved in acetone (3 mL) and the pH was adjusted to 7 by using acetic acid. Acetone was evaporated and the crude product was purified by chromatography on silica gel column (10×1 cm), eluting with DCM/methanol (1:1) to give 54 as a pale yellow oil: yield 14 mg (44%); silica gel TLC $R_f$ 0.12 (1:1 methanol-dichloromethane); $^1$H NMR (400 MHz, CDCl$_3$) δ 1.09-1.26 (m, 2H), 1.32-1.35 (m, 4H), 1.55-1.62 (m, 1H), 1.74-1.79 (m, 1H), 1.80-1.88 (m, 1H), 1.90-1.99 (m, 3H), 2.05-2.16 (m, 4H), 2.32-2.39 (m, 2H), 2.83 (brs, 2H), 3.07 (brs, 2H), 3.16-3.26 (m, 2H), 3.43 (brs, 2H), 3.50 (brs, 2H), 7.17 (dd, 1H, J=4.4, 7.6 Hz), 7.31 (brs, 1H), 7.61 (d, 1H, J=8.0 Hz), 8.39 (s, 1H) and 8.47 (s, 1H); $^{13}$C NMR (100 MHz, CDCl$_3$) δ 22.8, 24.8, 26.2, 28.5, 29.4, 35.3, 39.6, 52.7, 53.6, 54.3, 59.6, 67.7, 123.7, 135.3, 139.9, 148.4, 149.4, 168.6 and 173.7.

We claim:

1. A method for obtaining a nicotine hapten conjugate capable of eliciting an immune response specific to nicotine, the method comprising:
    (a) providing three-dimensional structural information of an immunogenic carrier, wherein the immunogenic carrier comprise one or more immunogenic carrier binding sites (ICBS);
    (b) selecting a functional group or small molecule fragment, wherein the selected functional group or small molecule fragment is:
        (i) predicted to bind to the one or more ICBS, and
        (ii) predicted to bind to free nicotine when bound to the one or more ICBS, and
        (iii) predicted to exhibit higher binding energy for free nicotine than for the immunogenic carrier; and
    (c) linking the selected functional group or small molecule fragment to nicotine or a nicotine derivative to create a nicotine hapten, and linking the nicotine hapten to the immunogenic carrier to create the nicotine hapten conjugate;
    (d) testing the nicotine hapten conjugates to determine an affinity index, and selecting the conjugate that elicits production of anti-nicotine antibodies having affinity index value greater than 0.02 and less than or equal to 1.

2. The method of claim 1, wherein the selecting of step (b) comprises using a computer having a non-transitory computer-readable storage medium containing programming to perform a fitting operation to determine one or more binding energy parameters of the functional group or small molecule fragment binding to free nicotine and the ICBS.

3. The method of claim 2, further comprising determining the higher binding energy by analyzing results of the fitting operation to characterize the association between (a) the functional group or small molecule fragment and free nicotine, and (b) the functional group or small molecule fragment and the one or more ICBS.

4. The method of claim 1, further comprising: (e) evaluating the nicotine hapten conjugate for its ability to compete with free nicotine for binding to an anti-nicotine antibody.

5. The method of claim 4, wherein evaluating comprises performing an indirect competitive enzyme-linked immunosorbent assay (ELISA).

6. The method of claim 1, wherein the immunogenic carrier is a streptavidin.

* * * * *

UNITED STATES PATENT AND TRADEMARK OFFICE
CERTIFICATE OF CORRECTION

PATENT NO. : 11,357,848 B2
APPLICATION NO. : 15/863118
DATED : June 14, 2022
INVENTOR(S) : Yung Chang et al.

It is certified that error appears in the above-identified patent and that said Letters Patent is hereby corrected as shown below:

In the Specification

Column 18, Line 36, "(MW)" should be --(MH$^+$)--.

Signed and Sealed this
Seventeenth Day of January, 2023

Katherine Kelly Vidal
*Director of the United States Patent and Trademark Office*